(12) United States Patent
Swartz et al.

(10) Patent No.: US 8,974,657 B2
(45) Date of Patent: Mar. 10, 2015

(54) AMPEROMETRIC ELECTROCHEMICAL CELLS AND SENSORS

(75) Inventors: Scott L. Swartz, Columbus, OH (US);
Matthew M. Seabaugh, Columbus, OH (US); Lora B. Thrun, Grove City, OH (US); Paul H. Matter, Columbus, OH (US); Michael J. Day, Dublin, OH (US); William J. Dawson, Dublin, OH (US); Buddy E. McCormick, Dublin, OH (US)

(73) Assignee: NexTech Materials Ltd., Lewis Center, OH (US)

( * ) Notice: Subject to any disclaimer, the term of this patent is extended or adjusted under 35 U.S.C. 154(b) by 0 days.

(21) Appl. No.: 12/875,407

(22) Filed: Sep. 3, 2010

(65) Prior Publication Data

US 2012/0055789 A1 Mar. 8, 2012

(51) Int. Cl.
*G01N 33/00* (2006.01)
*G01N 27/403* (2006.01)

(52) U.S. Cl.
CPC .......... *G01N 33/0054* (2013.01); *G01N 27/403* (2013.01); *G01N 33/0037* (2013.01)
USPC ....... 205/783.5; 204/424; 204/421; 73/23.31; 73/23.32

(58) Field of Classification Search
CPC .......... G01N 33/0054; G01N 33/0037; G01N 27/403
USPC ...................... 204/421–429; 73/23.31, 23.32; 205/783.5
See application file for complete search history.

(56) References Cited

U.S. PATENT DOCUMENTS 3,843,400 A * 10/1974 Radford et al. ............... 429/152
4,283,261 A * 8/1981 Maurer et al. ................ 204/408

(Continued)

OTHER PUBLICATIONS

Szabo et al, Solid State Ionics 171, 2004, pp. 183-190.*

(Continued)

*Primary Examiner* — Jennifer Dieterle
(74) *Attorney, Agent, or Firm* — Porter Wright Morris & Arthur LLP

(57) ABSTRACT

Amperometric ceramic electrochemical cells comprise, in one embodiment, an electrolyte layer, a sensing electrode layer comprising a ceramic phase and a metallic phase, and a counter electrode layer, wherein the cell is operable in an oxidizing atmosphere and under an applied bias to exhibit enhanced reduction of oxygen molecules at the sensing electrode in the presence of one or more target gases such as nitrogen oxides ($NO_x$) or $NH_3$ and a resulting increase in oxygen ion flux through the cell. In another embodiment, amperometric ceramic electrochemical cells comprise an electrolyte layer comprising a continuous network of a first material which is ionically conducting at an operating temperature of about 200 to 550° C.; a counter electrode layer comprising a continuous network of a second material which is electrically conductive at an operating temperature of about 200 to 550° C.; and a sensing electrode layer comprising a continuous network of a ceramic phase and a metallic phase which is electrically conductive at an operating temperature of about 200 to 550° C., which sensing electrode is operable to exhibit increased charge transfer in the presence of one or more target gas species. These electrochemical cells and additional electrochemical cell embodiments are suitable for use in gas sensors and methods of sensing or detecting one or more target gases.

30 Claims, 13 Drawing Sheets

(56) References Cited

U.S. PATENT DOCUMENTS

| | | | |
|---|---|---|---|
| 4,770,760 A * | 9/1988 | Noda et al. .................... | 204/425 |
| 5,021,137 A | 6/1991 | Joshi et al. | |
| 5,763,763 A | 6/1998 | Kato et al. | |
| 6,022,464 A | 2/2000 | Schumann | |
| 6,143,165 A * | 11/2000 | Kurosawa et al. ............ | 205/781 |
| 6,312,585 B1 * | 11/2001 | Wahl et al. ................. | 205/783.5 |
| 6,379,529 B1 * | 4/2002 | Wahl et al. ................. | 205/780.5 |
| 7,678,329 B2 | 3/2010 | Montgomery et al. | |
| 2001/0008211 A1 * | 7/2001 | Kato et al. .................... | 204/426 |
| 2002/0108871 A1 * | 8/2002 | Wang et al. ................... | 205/784 |
| 2003/0121801 A1 * | 7/2003 | Inaba et al. ................. | 205/785.5 |
| 2003/0205078 A1 * | 11/2003 | Hasei et al. .................. | 73/23.31 |
| 2004/0118703 A1 * | 6/2004 | Wang et al. ................... | 205/780.5 |
| 2006/0091022 A1 * | 5/2006 | Ruud et al. .................... | 205/775 |
| 2007/0193883 A1 * | 8/2007 | Garzon et al. ................ | 204/426 |
| 2008/0149499 A1 * | 6/2008 | Ding et al. ................. | 205/783.5 |

OTHER PUBLICATIONS

Reinhardt et al, Solid-State Sensors and Actuators, and Eurosensors IX, 1995, pp. 799-802.*

Reinhardt et al, Ionics, 1, 1995, pp. 32-39.*

Azad et al., Hydrocarbon and Sulfur Sensors for SOFC Systems Nov. 18, 2003.*

Dutta A et al: "Amperometric NOX sensor based on oxygen pumping current by using LaGaO3-based solid electrolyte for monitoring exhaust gas" Sensors and Actuators B, Elsevier Sequoia S.A., Lausanne, CH, vol. 108, No. 1-2, Jul. 22, 2005, pp. 309-313.

Sahibzada M et al: "Pd-promoted La0.6Sr0.4Co0.2Fe0.8O3 cathodes" Solid State Ionics, North Holland Pub. Company. Amsterdam, NL, vol. 113-115, Dec. 1, 1998, pp. 285-290.

Sabolsky E M et al: "Doped-CeO2 Thin-Film Ceramic Membranes for Small-Scale Oxygen Generation Systems" 2005 Aiche Spring National Meeting, Conference Proceedings, 2005, pp. 281-293.

Fergus et al: "Materials for high temperature electrochemical NOx gas sensors" Sensors and Actuators B, Elsevier Sequoia S.A., Lausanne, CH, vol. 121, No. 2, Feb. 3, 2007, pp. 652-663.

Zhuiykov et al: "Development of zirconia-based potentiometric NOx sensors for automotive and energy industries in the early 21st century: What are the prospects for sensors?" Sensors and Actuators B, Elsevier Sequoia S.A., Lausanne, CH, vol. 121, No. 2, Feb. 3, 2007, pp. 639-651.

Int'l Preliminary Report on Patentability, PCT App. No. PCT/US2009/035494, Aug. 31, 2010.

Office Action dated Jun. 6, 2012, for U.S Appl. No. 12/395,998.

Office Action dated Aug. 2, 2013, for U.S. Appl. No. 12/395,998.

* cited by examiner

AMPEROMETRIC ELECTROCHEMICAL CELLS AND SENSORS

FIELD OF THE INVENTION

This invention relates to amperometric ceramic electrochemical cells and sensors which, in specific embodiments, are suitable for detecting one or more target gas species, for example, nitrous oxides ($NO_X$) and/or ammonia, in a gaseous atmosphere such as in hydrocarbon combustion products, and to materials that enable functionality of these devices. In a specific embodiment, the cells and sensors of the invention may be used for $NO_X$ and/or $NH_3$ emissions detection in diesel fueled vehicles.

BACKGROUND OF THE INVENTION

The increase in worldwide industrialization has generated concern regarding pollution created by combustion processes. Particularly, emissions from vehicles or other distributed sources are of concern. New environmental regulations are driving $NO_X$ (a mixture of NO and $NO_2$ of varying ratio) emissions from diesel fueled vehicles to increasingly lower levels, with the most challenging of these being the 2010 EPA Tier 2 diesel tailpipe standards. To meet these, engine manufacturers have been developing new diesel after-treatment technologies including selective catalyst reduction (SCR) systems and lean $NO_X$ traps (LNT). See for example: T. Johnson, 2008 SAE International Proceedings, 2008-01-0069 (2008). These systems require multiple $NO_X$ sensors to monitor performance and satisfy on-board diagnostics requirements for tailpipe emissions. Point of generation abatement technologies have been developed for $NO_X$, among other pollutants, but these solutions can reduce fuel efficiency if they are applied without closed loop control. Further, some of the proposed solutions can be polluting (e.g. selective catalytic reduction systems for $NO_X$ can release ammonia into the atmosphere) if improperly controlled. Control of these abatement technologies requires the development of compact, sensitive sensors for $NO_X$ and other pollutants in oxygen-containing (lean-burn) exhaust streams.

Sensors that have been proposed to date cannot meet the requirements of the applications. The great majority of $NO_X$ detectors rely on the potentiometric or amperometric measurement of oxygen partial pressure (from the decomposition of $NO_2$ molecules to NO and NO to $N_2$ and $O_2$) to determine $NO_X$ concentration. This requires that the device be constructed with reference electrodes or reference pumping circuits to separate the $NO_X$ concentration from the background oxygen concentration.

Electrochemical sensors offer a means of measuring gas constituents in an analyte stream using a small, low power device. A number of electrochemical sensor approaches have been reported in the past. See for examples: J. W. Fergus, *Sensors and Actuators* B121, 652-663 (2007); W. Gopel, et al., *Solid State Ionics* 136-137, 519-531 (2000); and S. Zhuiykov, et al., *Sensors and Actuators* B 121, 639-651 (2007). These approaches range from potentiometric mixed potential sensors to impedance-based sensors to amperometric sensors. Most of these approaches employ a ceramic electrolyte material as one component of the device, with electrode materials that provide sensitivity to a gas species of interest. A broad scope of materials have been evaluated as the sensing and reference electrodes in these designs, including precious and base metals, as well as cermets, and both simple and complex oxides. The electrolyte selection has been much narrower, focusing principally on yttrium-stabilized zirconia and a minority of examples of NASICON electrolytes. None of these approaches meets all of the key requirements of the diesel exhaust application.

Mixed potential designs rely on the different kinetics of reaction to occur at the sensing and reference electrodes. For the example of $NO_X$ detection, two reactions are of interest:

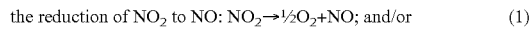
the reduction of $NO_2$ to NO: $NO_2 \rightarrow \frac{1}{2}O_2 + NO$; and/or (1)

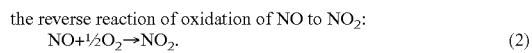
the reverse reaction of oxidation of NO to $NO_2$:
$NO + \frac{1}{2}O_2 \rightarrow NO_2$. (2)

These reactions occur at different rates over different electrode materials. The local liberation or consumption of molecular oxygen changes the oxygen partial pressure at the sensing electrode, and results in a change in the electromotive force (EMF) generated in contrast to the reference electrode. Reference electrodes are selected to be inert to these reactions but active for $O_2$ reduction (such as Au or Pt). Examples of sensing electrodes for mixed potential sensors include simple oxides such as $WO_3$, NiO, ZnO, $Cr_2O_3$, $V_2O_5$ or mixed oxides such as spinels composed of di- and trivalent transition metals, or lanthanide ferrite or chromite-based perovskites. Because the reference electrode compensates for oxygen that may be present in the gas stream, the EMF between the sensing and reference electrodes can be correlated directly with the concentration of NO or $NO_2$ present.

Drawbacks to the mixed potential approach include the interference of other gas species with the sensing and reference electrodes. Reducing gases present in the gas stream, such as hydrocarbons and CO, will interfere with the signal. Another complexity of mixed potential devices is that the catalytic reaction between NO and the sensing electrode consumes oxygen, resulting in a negative relative EMF, while the reduction of $NO_2$ generates a positive EMF through the liberation of $O_2$ causing inaccurate measurement of total $NO_X$ concentration.

A number of strategies have been proposed to overcome these limitations. Protective zeolite coatings have been used, which allow gas molecules of only a particular size to pass through to the sensing element, barring the combustion products, hydrocarbons and particulates from affecting the measurement. Alternatively, selective sensing electrode materials may be employed which favor only the oxidation or reduction reaction (such as $LaCoO_3$, which has been identified to be responsive to $NO_2$ but not NO) allowing arrays of mixed potential sensors to be used to determine the NO and $NO_2$ concentration. Similarly, a non-selective sensing electrode can be biased at different voltages to produce an array of sensors which can be simultaneously solved to determine NO and $NO_2$ concentration.

A fundamental concern in the development of mixed potential sensors is that the sensing electrode microstructure controls the non-equilibrium oxygen partial pressure and the kinetics that generate the mixed-potential response. It has also been suggested that microstructure control through the development of multi-component nanocomposite electrodes may allow development of sufficiently responsive and stable electrode materials, but at this time, such devices have not been demonstrated.

Amperometric designs measure the current resulting from a constant applied voltage on an electrochemical cell. A number of amperometric sensor designs have been reported in the literature. Electrolytes of these designs are limited to NASICON, YSZ, and lanthanum gallate electrolytes, operating at temperatures ranging from below 200° C. for NASICON to above 500° C. for the YSZ and lanthanum gallate electrolytes.

Amperometric designs as reported in the literature have commercial viability, as will be discussed below. However, they must overcome the limited current that can be achieved by conventional approaches. The devices disclosed in the literature rely upon the catalytic decomposition of $NO_X$ to provide the detected current under the imposed voltage, as shown by the following equations:

the reduction of $NO_2$ to $NO$: $NO_2 \rightarrow +\frac{1}{2}O_2 + NO$, and/ or (3)

the reduction of $NO$ to $N_2$ and $O_2$: $NO \rightarrow \frac{1}{2}N_2 + \frac{1}{2}O_2$. (4)

Due to the very low concentrations of $NO_X$ anticipated in the applications, the signals achieved by these devices are extremely low, limiting the resolution, accuracy, and detection threshold of these sensors. For tailpipe emissions monitoring of $NO_X$ in diesel vehicles, accurate detection of low ppm concentrations of $NO_X$ is essential to meeting emissions regulations. Additionally, these low signals require additional shielding to protect from electromagnetic interference.

Impedance-based sensors are the third class of electrochemical devices that have been proposed for NOx sensing applications. In these devices, an oscillating voltage is applied to the sensing electrodes, and the current generated by the voltage is measured. By tailoring the frequency of the voltage oscillations, the response can be selected to correlate with specific non-ohmic contributions to the device resistance. In this approach, the divergent responses of NO and $NO_2$ in mixed potential mode are not observed; instead, signals of the same sign and magnitude are observed. However, these devices are the earliest in development and experience interference from both $CO_2$ and $H_2O$, which will always be present in exhaust streams. Finally, even under simplified operating conditions, impedance-based sensors will require more complex signal processing than mixed potential or amperometric sensors.

Several of the above sensor design approaches have been described in the technical and patent literature. One such device is a multi-chamber potentiometric device, which uses a multi-stage reaction approach to condition the exhaust stream for $NO_X$ detection. See for examples: U.S. Pat. No. 5,861,092; U.S. Pat. No. 5,897,759; U.S. Pat. No. 6,126,902; U.S. Pat. No. 6,143,165; U.S. Pat. No. 6,274,016; and U.S. Pat. No. 6,303,011. In an initial reaction chamber, oxygen from an external air stream is pumped into the measurement chamber to oxidize all residual hydrocarbons and carbon monoxide, and convert the NO to $NO_2$. The resultant test stream is then exposed to a mixed potential sensing and reference electrode set. The resulting potential is measured to determine $NO_X$ concentration. Given the delay for the required processing of the sample gas, the response time of the sensor is anticipated to be too long (several seconds) for use in vehicle applications.

A second mixed potential sensor using yttria-stabilized zirconia (YSZ) with a zeolite-modified electrode, has been studied for $NO_X$ detection. See for examples: U.S. Pat. No. 6,764,591; U.S. Pat. No. 6,843,900; and U.S. Pat. No. 7,217,355. This device only works well at high temperatures, is very sensitive to changes in temperature, and has response times of two seconds or more. Due to the slow response times, this technology has not been employed for mobile applications.

The most prominent sensor type for detecting $NO_X$ is an amperometric device relying upon multiple oxygen ion pumps, developed and patented by NGK Insulators in Japan. See for example: U.S. Pat. No. 4,770,760 and U.S. Pat. No. 5,763,763. In this technology, considered by engine manufacturers to be the principal viable commercial $NO_X$ sensor, all the molecular oxygen in the exhaust gas stream is electrochemically pumped from the exhaust gas sample, before the remaining $NO_X$ can be reduced to $N_2$ and $O_2$ by a catalytic electrode material (typically a Pt/Rh alloy) and the resulting oxygen ionic current measured. These sensors are relatively slow, complex, costly, and cannot sense the low $NO_X$ concentrations needed by the diesel engine industry. Additionally, they exhibit a strong cross-sensitivity to ammonia, causing erroneous $NO_X$ measurements in ammonia-containing gas environments. To effectively monitor $NO_X$ breakthrough in either selective catalytic reduction or lean $NO_X$ trap systems, resolution of at least 5 ppm and preferably 3 ppm is needed compared to the 10 ppm accuracy of the NGK sensor.

In other research (see for example G. Reinhardt, et al., *Ionics* 1, 32-39 (1995)), NO is reported to assist in the electrochemical reduction of oxygen, forming the basis of an amperometric sensor. Because of the electrode and electrolyte materials used, however, the demonstrated cell required a minimum operating temperature of 600° C. At these higher temperatures, $O_2$ and $CO_2$ adsorption are thermodynamically favored over $NO_X$ adsorption. See: P. Broqvist, et al., *Journal of Physical Chemistry B*, 109:9613-9621 (2005). Consequently, Reinhardt and his co-workers did not demonstrate $NO_X$ sensitivity in the presence of $CO_2$ or water or at low $NO_X$ concentrations, and only demonstrated detection of $NO_X$ at high temperatures in simplified gas atmospheres. For operation in diesel engine exhaust systems, the ability to detect ppm levels of $NO_X$ in the presence of $CO_2$ and $H_2O$ is essential, making this approach impractical for use in these applications.

Accordingly, a need exists for improved sensors for accurately detecting $NO_X$ or other target gas species.

SUMMARY OF THE INVENTION

The electrochemical cells and sensors of the present invention, and methods employing the same, overcome various limitations of the above-described approaches. This invention is directed to electrochemical cells and sensors for, inter alia, detecting engine emissions in the oxygen-containing environment of a combusted hydrocarbon fuel exhaust, using an electro-catalytic effect. The electrochemical cells and sensors of the invention can operate in combustion exhaust streams with significantly enhanced sensitivity to both $NO_X$ and ammonia ($NH_3$), with less dependence on oxygen partial pressure, with a faster response, and at lower temperatures than various sensors of the prior art.

The electrochemical cells and sensors of the invention are distinguishable from various known sensors due to the mechanism employed to detect gas constituents and the temperature at which the electrochemical cells and sensors operate. The electrochemical cells and sensors are configured as amperometric devices but respond when adsorbed gas species increase the rate of oxygen reduction on the sensing electrode of the devices. The electrochemical cells and sensors do not require catalytic $NO_X$ decomposition to sense the $NO_X$ concentration and, rather, use an increase in oxygen reduction current, caused by the presence of adsorbed $NO_X$, to detect $NO_X$ in an oxygen-containing gas stream. This mechanism is extremely fast compared to various competing sensor technologies and produces a current greater than what is possible from the reduction of $NO_X$ alone. Further, this catalytic approach has been demonstrated to extend to other gaseous species, including $NH_3$.

The amperometric cells and sensors are based on an oxygen ion conducting cell, but unlike conventional sensors, this approach does not rely on the oxygen ion current resulting from the direct decomposition of $NO_X$ in the gas stream as the response signal. In specific embodiments, Perovskite electrodes, such as $(La_{1-X}Sr_X)(Co_{1-Y}Fe_Y)O_{3-\delta}$ (LSCF), where X ranges from approximately 0.2 to 0.4 and Y ranges from approximately 0.2 to 0.4, when applied to an oxygen ion ($O^{2-}$) conducting electrolyte show catalytic activity for $O_2$ reduction in the presence of $NO_X$ and/or $NH_3$. Other electrode material compositions also have been shown to provide catalytic activity for $O_2$ reduction in the presence of $NO_X$ and/or $NH_3$, as will be disclosed. In this novel approach, the cells and sensors detect $NO_X$ and $NH_3$ through a catalytic effect, in which the reduction of oxygen in the gas stream is catalyzed by the presence of $NO_X$ and $NH_3$ species on the surface of such an electrode. This results in a device with particular advantages in design simplicity and flexibility, materials selection, and operating conditions in contrast to previously disclosed sensors. The cells and sensors also are responsive to $NO_X$ in the presence of steam, carbon dioxide and sulfur oxides ($SO_X$). The cells and sensors have a tunable response to $NH_3$, which allows only $NO_X$ to be detected or both $NO_X$ and $NH_3$ to be detected and quantified at the same time. Specific sensor embodiments have been demonstrated to detect NO and $NO_2$ at levels as low as 3 ppm and/or to exhibit sensor response as fast as 50 ms, allowing for better system controls or even engine feedback control. Further, in certain embodiments, the disclosed cells and sensors operate in a temperature range of 200 to 550° C., over which the $NO_X$ and $NH_3$ responses are significantly greater than the sensitivity to variable background exhaust gases.

While the cells and sensors of the present invention have applicability to detection of $NO_X$ in heavy duty diesel exhaust systems, the same may be useful in a wide range of other applications in which rapid response to low levels of $NO_X$ is desired. The $NO_X$ cells and sensors are particularly useful in sensing low levels of $NO_X$ in the presence of fixed or variable concentrations of other gases, including without limitation $O_2$, $CO_2$, $SO_X$ (SO and/or $SO_2$), $H_2O$, and $NH_3$. Further, the cells and sensors formulation, operating temperature, and applied voltage can be tuned to be responsive to other gases that alter oxygen reduction activity of the sensing electrode, including without limitation $SO_X$, $O_2$, $NH_3$, and $CO_2$. Cells and sensors tailored to the detection of low levels of these gases also may be useful in a wide range of applications.

Various embodiments, features and advantages of the invention will be more fully understood in view of the following detailed description.

BRIEF DESCRIPTION OF THE DRAWINGS

Sensors of the present invention are described with reference to several figures, in which.

Figure 1:
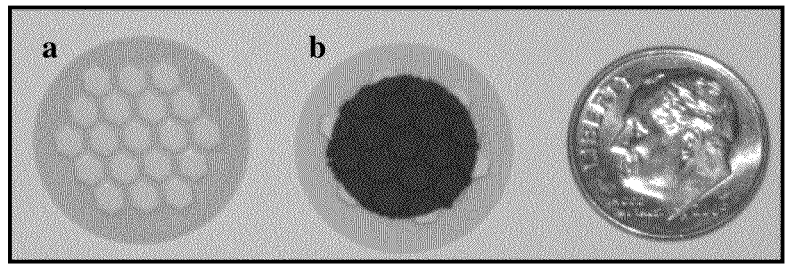
FIG. 1 is a photograph of the sensor design of Example 1 showing: (a): gadolinium doped ceria ceramic electrolyte membrane disc, without electrodes; and (b) ceramic electrolyte disc with $(La_{0.6}Sr_{0.4})(Co_{0.2}Fe_{0.8})O_{3-\delta}$ (LSCF) electrodes, applied to opposite faces of the electrolyte disc.

These Figures demonstrate various features and embodiments of cells and sensors of the present invention, and methods employing the same, but are not to be construed as limiting of the invention.

DETAILED DESCRIPTION OF THE INVENTION

The electrochemical cells and sensors of the present invention are described herein and in the following examples by reference to a limited range of electrolyte, electrode, optional catalytic materials, promoters, filter materials, and protective adsorbents. However, it is apparent in view of the present specification that the electrochemical cells and sensors will yield acceptable results with a wide range of such materials. In addition, while exemplary electrolyte and electrode film thickness are described, the invention includes all film thicknesses having acceptable mechanical integrity and electrochemical response.

In one embodiment, the invention is directed to an amperometric ceramic electrochemical cell comprising an electrolyte layer, a sensing electrode layer, and a counter electrode layer. The cell is operable in an oxidizing atmosphere and under an applied bias to exhibit enhanced reduction of oxygen molecules at the sensing electrode in the presence of one or more nitrogen oxides ($NO_X$) and/or ammonia ($NH_3$) and a resulting increase in oxygen ion flux through the cell. The sensing electrode and counter electrode may be made of the same or different materials, as will be set forth in further detail below. Additionally, the counter electrode can be exposed to the same gas environment as the sensing electrode, so that there is no requirement for an oxygen reference when the electrochemical cell is employed in a sensor. This provides a significant advantage over many sensors which require an oxygen reference. The counter electrode can be exposed to air as well, or, if desired, oxygen reference electrode can be provided in a sensor employing the inventive cell. In one embodiment, the cell is operable to exhibit the enhanced reduction of oxygen molecules at the sensing electrode in the presence of one or more nitrogen oxides and a resulting increase in oxygen ion flux through the cell in proportion to a concentration of nitrogen oxides in the oxidizing atmosphere. In another embodiment, sensor is operable to exhibit at least sixty percent of its equilibrium response to the presence of nitrogen oxides in less than one minute, or more specifically in less than one second, or more specifically in less than 200 milliseconds. The invention is also directed to sensors employing such cells.

In another embodiment, the invention is directed to an amperometric ceramic electrochemical cell comprising an electrolyte layer comprising a continuous network of a first material which is ionically conducting at an operating temperature of about 200 to 550° C.; a counter electrode layer comprising a continuous network of a second material which is electrically conducting at an operating temperature of about 200 to 550° C.; and a sensing electrode layer comprising a continuous network of a third material which is electrically conducting at an operating temperature of about 200 to 550° C., which sensing electrode is operable to exhibit increased charge transfer in the presence of one or more target gas species. In one embodiment, the electrolyte layer first material is oxygen ion conducting at the specified operating temperature. In a further embodiment, the electrolyte layer prevents physical contact between the counter electrode layer and the sensing electrode layer, and the cell is operable to exhibit conductivity to oxygen ions at an operating temperature of about 200 to 550° C. and increased or decreased resistance in the presence of the one or more target gas species. The invention is also directed to sensors employing such cells. In one such sensor, the sensor is operable to generate an electrical signal as a function of target gas concentration in an oxygen-containing gas stream, in the absence of additional sensing electrodes or oxygen pumping currents.

In yet another embodiment, the invention is directed to electrochemical cell for the amperometric detection of one or more gas species. The cell comprises an ionically conducting electrolyte membrane, a sensing electrode comprising an electrically conducting ceramic, and a counter electrode comprising an electrically conducting ceramic, cermet or metal, wherein the electrochemical cell is operable to pass current by reduction of oxygen at the sensing electrode, transport of oxygen ions through the electrolyte, and recombination of oxygen ions at the counter electrode layer. In specific embodiments, the sensing electrode is operable to exhibit varying catalysis of oxygen reduction in the presence of $NO_X$ (one or more oxides of nitrogen), CO, $CO_2$, and/or $SO_X$ (one or more oxides of sulfur), or, more specifically, the sensing electrode is operable to exhibit reversible adsorption of NO and $NO_2$ and varying catalysis of oxygen reduction in the presence of $NO_X$, CO, $CO_2$, and/or $SO_X$.

In additional embodiments, the invention is directed to an electrochemical cell for the amperometric detection of gas species comprising (a) an ionically conducting electrolyte comprising cerium oxide doped with Ca, Sr, Sc, Y, Pr, Nd, Pm, Sm, Eu, Gd, Tb, Dy, Ho, Er, Tm, Yb, La, or a mixture thereof; zirconium oxide doped with Ca, Mg, Sc, Y, Ce, or a mixture thereof; bismuth oxide doped with Y, V, Cu, Er or a mixture thereof; or lanthanum gallium oxide doped with Sr, Mg, Zn, Co, Fe or a mixture thereof; (b) a sensing electrode comprising lanthanide manganite perovskite material, doped with Ca, Sr, Ba, Fe, Co, Ni, Cu, Zn, Mg or a mixture thereof; lanthanide ferrite perovskite material, doped with Ca, Sr, Ba, Mn, Co, Ni, Cu, Zn, Mg or a mixture thereof; lanthanide cobaltite perovskite material, doped with Ca, Sr, Ba, Mn, Fe, Ni, Cu, Zn, Mg or a mixture thereof; lanthanide nickelate perovskite material, doped with Ca, Sr, Ba, Mn, Fe, Co, Cu, Zn, Mg or a mixture thereof; lanthanide cuprate perovskite material, doped with Ca, Sr, Ba, Mn, Fe, Co, Ni, or a mixture thereof; a composite material comprising a mixture of ceramic and metallic phases (cermet), where the ceramic phase is a ceramic electrolyte material, for example, a zirconia-based electrolyte material, a ceria-based electrolyte material, a bismuth oxide-based electrolyte material or a lanthanum gallium oxide-based electrolyte material, or a mixture thereof, and the metallic phase comprises Ag, Pt, Pd, Rh, Ru, Ir or an alloy or mixture thereof; a composite material comprising a mixture of ceramic and metallic phases, where the ceramic phase is an insulator such as aluminum oxide, magnesium oxide, or another insulating ceramic material, and the metallic phase comprises Ag, Pt, Pd, Rh, Ru, Ir or an alloy or mixture thereof; a metallic electrode material comprising Ag, Pt, Pd, Rh, Ru, Ir or an alloy or mixture thereof; or a mixture comprising two or more of any of the above-mentioned sensing electrode materials; (c) a counter electrode comprising lanthanide manganite perovskite material, doped with Ca, Sr, Ba, Fe, Co, Ni, Cu, Zn, Mg or a mixture thereof; lanthanide ferrite perovskite material, doped with Ca, Sr, Ba, Mn, Co, Ni, Cu, Zn, Mg or a mixture thereof; lanthanide cobaltite perovskite material, doped with Ca, Sr, Ba, Mn, Fe, Ni, Cu, Zn, Mg or a mixture thereof; lanthanide nickelate perovskite material, doped with Ca, Sr, Ba, Mn, Fe, Co, Cu, Zn, Mg or a mixture thereof; lanthanide cuprate perovskite material, doped with Ca, Sr, Ba, Mn, Fe, Co, Ni, or a mixture thereof; or a metal material comprising Ni, Fe, Cu, Ag, Au, Pd, Pt, Rh, or Ir, or an alloy, a mixture or a cermet thereof.

In a specific embodiment of such an electrochemical cell, the electrolyte comprises ionically conducting cerium oxide doped with Ca, Sr, Sc, Y, Pr, Nd, Pm, Sm, Eu, Gd, Tb, Dy, Ho, Er, Tm, Yb, La or a mixture thereof; the sensing electrode material comprises lanthanide ferrite perovskite material doped with Ca, Sr, Ba, Mn, Co, Ni, Cu, Zn, Mg or a mixture thereof, or lanthanide cobaltite perovskite material doped with Ca, Sr, Ba, Mn, Fe, Ni, Cu, Zn, Mg or a mixture thereof; and the counter electrode material comprises lanthanide ferrite perovskite material doped with Ca, Sr, Ba, Mn, Co, Ni, Cu, Zn, Mg or a mixture thereof, lanthanide cobaltite perovskite material doped with Ca, Sr, Ba, Mn, Fe, Ni, Cu, Zn, Mg or a mixture thereof, or a metal material comprising Ni, Fe, Cu, Ag, Au, Pd, Pt, Rh, or Ir, or an alloy, a mixture or cermet thereof. In a more specific embodiment, the electrolyte is ionically conducting and comprises cerium oxide doped with Y, Nd, Sm, Gd, La or mixtures thereof; the sensing electrode is ionically and electronically conducting and comprises Sr and Co doped lanthanide ferrite, and the counter electrode is electronically conducting. In another embodiment, the electrolyte is ionically conducting and comprises Sm-doped cerium oxide electrolyte; the sensing electrode is ionically and electronically conducting and comprises Lanthanum Strontium Cobalt Ferrite, and the counter electrode is an electrically conducting and comprises Lanthanum Strontium Cobalt Ferrite.

In another specific embodiment, the electrolyte is ionically conducting and comprises Gd-doped cerium oxide electrolyte; the sensing electrode is ionically and electronically conducting and comprises Lanthanum Strontium Cobalt Ferrite, and the counter electrode is an electrically conducting material. In yet another specific embodiment, the electrolyte comprises either Gd-doped ceria or Sm-doped ceria; the sensing electrode comprises Lanthanum Strontium Cobalt Ferrite, Lanthanum Strontium Zinc Ferrite, a cermet mixture of Gd-doped ceria and Platinum, a cermet of Sm-doped ceria and Platinum, a cermet of Gd-doped ceria and Palladium, or a cermet of Sm-doped ceria and palladium; and the counter electrode is an electrically conducting material.

In additional embodiments of the various electrochemical cells of the invention, suitable electrolyte materials for the disclosed cells and sensors may include gadolinium-doped ceria (GDC or $Ce_{1-X}Gd_XO_{2-X/2}$, where X ranges from approximately 0.05 to 0.40) or samarium doped ceria (SDC or $Ce_{1-X}Sm_XO_{2-X/2}$, where X ranges from approximately 0.05 to 0.40) including but not limited to the compositions described herein. Other ceramic electrolyte materials also may be suitable, including yttrium doped ceria (YDC), cerium oxide doped with other lanthanide elements or cerium oxide doped with two or more lanthanide or rare earth elements. Still other suitable electrolyte materials for the disclosed sensor may include: fully or partially doped zirconium oxide including but not limited to yttrium stabilized zirconia (YSZ) and scandium doped zirconia (ScSZ); alkaline earth zirconates and cerates; doped bismuth oxides, lanthanum gallate based ceramic electrolytes, such as $(La_{1-X}Sr_X)(Ga_{1-Y}Mg_Y)O_{3-X/2-Y/2}$, where X ranges from approximately 0.05 to 0.30 and Y ranges from approximately 0.05 to 0.30; other ceramic materials that conduct electricity predominantly via transport of oxygen ions; mixed conducting ceramic electrolyte materials; proton conducting electrolyte materials; and/or mixtures thereof. An interfacial layer of GDC, SDC or another suitable electrolyte material may be provided between an electrolyte substrate and electrode layers. Further sensing electrodes could be deposited onto a GDC, SDC or other suitable electrolyte material that is first deposited onto an aluminum oxide ceramic substrate or any other ceramic substrate material that is not an electrolyte material.

The sensing electrode may be a perovskite electrode composition having the general formula: $(A_{1-X}A'_X)_{1-Z}(B_{1-Y}B'_Y)O_{3-\delta}$, where A is a tri-valent lanthanide element and A' is a bi-valent rare-earth element. Suitable electrode materials may include $(La,Sr)(Co,Fe)O_3$ (LSCF) compositions, including but not limited to the specific compositions described herein. Other suitable electrode materials may include (La, Sr)(Mn)O$_3$ (LSM), $(La,Sr)FeO_3$ (LSF), $(La,Sr)CoO_3$ (LSC), LaNiO$_3$, $(La,Sr)CuO_{2.5}$ (LSCu), $(Sm,Sr)CoO_3$ (SSC), (Pr,Sr)MnO$_3$ (PSM), $(Pr,Sr)FeO_3$ (PSF), $(Pr,Sr)CoO_3$ (PSC), $La(Mn,Co)O_3$ (LMC), $La(Ni,Mn)O_3$ (LNM), $La(Ni,Co)O_3$ (LNC) and $La(Ni,Fe)O_3$ (LNF). Suitable electrode materials also may be variants of the above electrode materials families listed above whereby lanthanum is replaced fully or partially by yttrium or the lanthanide series of cations, Sr is replaced fully or partially by the alkaline earth series of cations, examples including but not limited to $(Ba,Sr)(Co,Fe)O_3$ (BSCF). Suitable electrode materials also may be variants whereby solid solutions of the electrode families listed above are produced, for examples: $(La,Sr)(Mn,Co)O_3$ (LSMC), $(Pr,Sr)(Mn,Co)O_3$ (PSMC), and $(Pr,Sr)(Mn,Fe)O_3$ (PSMF). Further, suitable electrode materials may be doped versions of the above listed electrode materials families in which other transition metals are doped onto the B-site of the structure, for examples: $(La,Sr)(Zn,Fe)O_3$ (LSZF), $(La,Sr)(Mg,Fe)O_3$ (LSMgF), (La,Sr)(Ni,Fe)$O_3$ (LSNF), and (La,Sr)(Cu,Fe)$O_3$ (LSCuF). Further, non-perovskite electrode materials may be suitable, including layered perovskites, brownmillertites and other derivative structures, including but not limited to yttrium barium copper oxide (YBCO), $La_2NiO_4$, and $GdBaCuO_5$, $Sr_2Co_2O_5Sr_2Fe_2O_5Sr_2FeCoO_5$, and $Sr_2Mn_2O_5$.

The sensing electrode may also be a composite electrode comprising an electrode material (any of the above described electrodes) and an electrolyte material (any of the above described electrolyte formulations), or a composite between a metal (Ag, Au, Pd, Pt, Rh or Ir, or an alloy or mixture thereof) and an electrolyte material (any of the above described electrolyte formulations).

The counter electrode composition may be the same as the sensing electrode composition, or the counter electrode may have a different composition from the sensing electrode. Suitable counter electrodes include those materials listed above, as well as any of the following: Ag, Au, Pt, Pd, Ru, Ir, Rh, mixtures or alloys thereof, or any other conductive material known to catalyze the re-oxidation of oxygen ions to molecular oxygen.

Catalytic or electrocatalytic promoters may be included in the electrodes, particularly the sensing electrode, to improve performance. Such promoters which may optionally be incorporated into the electrode material to improve performance may include, but are not limited to, the following or any combination of the following: Ag, Au, Pt, Pd, Ru, Ir, Ni, Fe, Cu, Sn, V, Rh, Co, W, Mo, U, Zn, Mn, Cr, Nb or other compositions known to catalyze oxidation of hydrocarbons, CO, $NH_3$, carbon, and other reductants that may interfere with sensor response. If the promoter is catalyzing carbon oxidation, the promoter will also assist in protecting the sensor from fouling. In additional embodiments, the promoter may comprise cerium or doped cerium oxide, an alkali metal, or an alkaline earth metal. Additionally, in specific embodiments, the promoter may be added to equilibrate the NO to $NO_2$ ratio in the gas stream, to promote $NO_X$ or $NH_3$ adsorption, i.e., the capacity or rate of $NO_X$ or $NH_3$ adsorption, to oxidize NO to $NO_2$, or to selectively enhance oxygen reduction in the presence of $NO_X$.

Promoters that may be added to enhance the capacity or rate of $NO_X$ adsorption, include but not limited to potassium, barium, sodium, lanthanum, calcium, strontium, magnesium, and lithium or other alkali or alkaline earth metals and any combination of these materials. Promoters may also be added to decrease electrical resistance of the cell in the absence of $NO_X$, i.e., to reduce oxygen reduction on the sensor electrode in the absence of $NO_X$, thus improving $NO_X$ selectivity over the operating range of the sensor (temperature, voltage, etc.). In this embodiment, the promoter can be viewed as an inhibitor. Such promoters include, but are not limited to, chlorine, fluorine, potassium, barium, sodium, calcium, lanthanum, strontium, magnesium, and lithium or any combination of these materials. Promoters may also be added to enhance selectivity to $SO_X$, $NH_3$, or other gases to tune the sensor to detection of these gases.

Sensors of different formulations could be coupled to detect multiple gases and provide enhanced selectivity. For example, a $Gd_XCe_{1-X}O_{2-X/2}$ (GDC), ceramic electrolyte membrane with $La_{1-X}Sr_XFe_{1-Y}Co_YO_{3-\delta}$ (LSCF) electrodes has greater sensitivity to $NO_X$ than to $NH_3$. By combining these sensors with the appropriate electronics, the responses to both $NO_X$ and ammonia can be discerned.

Filter materials and/or protective adsorbent materials may be added to protect the sensor from poisons in the exhaust stream including particulate matter, soot, sulfur compounds, silicon compounds, engine oil contaminants such as phosphorous, zinc, and calcium compounds, lead, road salt, and other application contaminants. These protective materials may be added to the electrode or electrolyte material composition, may be infiltrated into the electrode layer, or may be applied as a coating onto the electrode layer. In a specific embodiment, a protective material is printed on the cell to cover the electrodes. These materials may be porous in structure and include, but are not limited to, zeolite materials, aluminum oxide, electrolyte materials (as listed above), molybdenum oxide, zinc oxide, tungsten oxide or any other materials that provide a physical or chemical filter and/or have an affinity to preferentially adsorb these contaminants.

For optimum $NO_X$ selectivity, the sensor is operated in the range of 200 to 550° C. with an applied bias of from about 0.01 to about 1 volt, or, in more specific embodiments, with an applied bias of about 0.05 to about 0.4 volts, or with an applied bias of about 0.1 to about 0.5 volts. The operating temperature range may be modified to achieve improved selectivity to other gases such as ammonia, $SO_2$, $CO_2$ and $O_2$. Additionally the applied voltage may be constant or varying. In a specific embodiment, the sensor is operated with a constant applied bias in the indicated ranges. Alternatively, the sensor may be operated with an applied bias that is modified either to a different range or to an alternating polarity mode, whereby the voltage is cycled between a negative applied voltage and positive applied voltage. The frequency of this cycling may also be adjusted to enhance sensitivity, selectivity, and poison resistance of the sensor. The sensor may also be periodically exposed to a different set of operating conditions such as higher temperature or applied voltage, or a cycled voltage to remove and/or prevent poisoning from sulfur, silica, hydrocarbon particulate matter, or other contaminants. For example, a sensor device can be constructed with two different electrode materials, one that is sensitive to $NO_X$ and a second that is sensitive to $NH_3$, and by alternating the polarity and/or magnitude of the applied voltage across the electrodes, both $NO_X$ and $NH_3$ can be measured in a single sensor.

In a specific embodiment, an electrochemical cell comprising an electrolyte layer, a sensing electrode layer, and a counter electrode layer, according to the invention is operable in an oxidizing atmosphere and under a first applied bias to exhibit enhanced reduction of oxygen molecules at the sensing electrode in the presence of one or more nitrogen oxides ($NO_X$) and a resulting increase in oxygen ion flux through the cell and is operable in the oxidizing atmosphere and under a second applied bias different from the first applied bias to exhibit enhanced reduction of oxygen molecules at the sensing electrode in the presence of $NH_3$ and a resulting increase in oxygen ion flux through the cell. In another embodiment, an electrochemical cell comprising an electrolyte layer, a first electrode layer, and a second electrode layer according to the invention is operable in an oxidizing atmosphere and under a first applied bias to exhibit enhanced reduction of oxygen molecules at the first electrode in the presence of one or more nitrogen oxides ($NO_X$) and a resulting increase in oxygen ion flux through the cell and is operable in the oxidizing atmosphere and under a second applied bias different from the first applied bias to exhibit enhanced reduction of oxygen molecules at the second electrode in the presence of $NH_3$ and a resulting increase in oxygen ion flux through the cell. Alternatively, a sensor may include a combination of cells according to the invention. In a specific embodiment of such, a sensor comprises (a) a first amperometric ceramic electrochemical cell comprising an electrolyte layer, a sensing electrode layer, and a counter electrode layer, wherein the cell is operable in an oxidizing atmosphere and under a first applied bias to exhibit enhanced reduction of oxygen molecules at the sensing electrode in the presence of one or more nitrogen oxides ($NO_X$) and a resulting increase in oxygen ion flux through the cell and is operable in the oxidizing atmosphere; and (b) a second amperometric ceramic electrochemical cell comprising an electrolyte layer, a sensing electrode layer, and a counter electrode layer, wherein the cell is operable under a second applied bias different from the first applied bias to exhibit enhanced reduction of oxygen molecules at the sensing electrode in the presence of $NH_3$ and a resulting increase in oxygen ion flux through the cell.

The cells and sensors of the invention may be configured to be compatible with various application environments, and may include substrates with modifications to provide structural robustness, addition of a heater to control sensor temperature, modifications to the electrolyte geometry and overall sensor size and shape, external packaging and shielding to house and protect the sensor, and appropriate leads and wiring to communicate the sensor signal to the application. The sensor technology is applicable to both planar and tubular geometries. Additionally, multiple electrochemical cells with different electrode formulations may be employed in a single sensor device to enable detection of multiple gas species. Electrodes may be located on the same side or on opposing sides of the electrolyte later. Additionally, the sensor may comprise multiple electrochemical cells to increase signal levels. Exemplary embodiments include, but are not limited to, electrochemical cells and sensors wherein the electrode layers are symmetrically opposed to one another on each side of the electrolyte layer, whereby oxygen ion current flows through a thickness of the electrolyte; wherein the electrode layers are laterally spaced on a single surface of the electrolyte layer, with an uncoated area of the surface of the electrolyte layer between the electrode layers; wherein the electrode layers are interspaced to form an interdigitated or interlocking design of electrodes of opposite polarity while maintaining a minimal electrode path length therebetween; and/or wherein the electrolyte layer has a hollow tubular configuration, and the electrode layers are applied internally and/or externally to the electrolyte layer. In one configuration, the electrolyte is a porous component and prevents physical contact between the electrode layers.

A substrate may be included in the sensors of the invention, in combination with the described electrochemical cells, for example to provide mechanical support, and may comprise any suitable insulating material, for example, an insulating ceramic or a metal or cermet material coated with an insulating material. In one embodiment, a sensor includes a zirconia substrate, or more specifically, a yttrium-stabilized zirconia (YSZ) substrate. The sensor may optionally include a heater which is electrically isolated from the electrolyte and electrodes. The heater may be a resistive heater formed, for example, from a conductive metal such as, but not limited to, platinum, silver, or the like. The heater may, for example, be applied to or embedded in the substrate, or applied to the cell through another insulating layer such as aluminum oxide.

Various features and advantages of the amperometric sensor described in this invention will become evident from the devices and results obtained as described under the following Examples.

Example 1

Sensor Fabrication and Testing Method

Symmetrically electroded electrolyte membrane discs were used to test the fundamental sensing properties of this invention and confirm the sensing mechanism, as will be described in Examples 2 through 7. Planar electrochemical cells were fabricated using a gadolinium doped ceria ($Ce_{0.9}Gd_{0.1}O_{1.95}$, GDC) electrolyte membrane with ($La_{0.60}Sr_{0.40}$)($Co_{0.20}Fe_{0.80}$)$O_{3-\delta}$ (LSCF) electrodes applied to opposite sides. The electrolyte membrane in a disc form, shown in FIG. 1a, consists of a self-supporting electrolyte membrane of GDC, with an effective thickness of 40 microns. As disclosed in U.S. patent application Ser. No. 11/109,471 (published Oct. 19, 2006 as US 2006/0234100 A1), incorporated herein by reference in its entirety, the membrane is mechanically supported by an additional thicker doped ceria layer, in a perforated design approximately 100 microns thick which is simultaneously sintered with the membrane layer. As shown in FIG. 1b, the active area of the sensor is defined by the area of the deposited electrodes, which are symmetrically deposited on the opposite sides of the membrane disc and then annealed.

Figure 2:
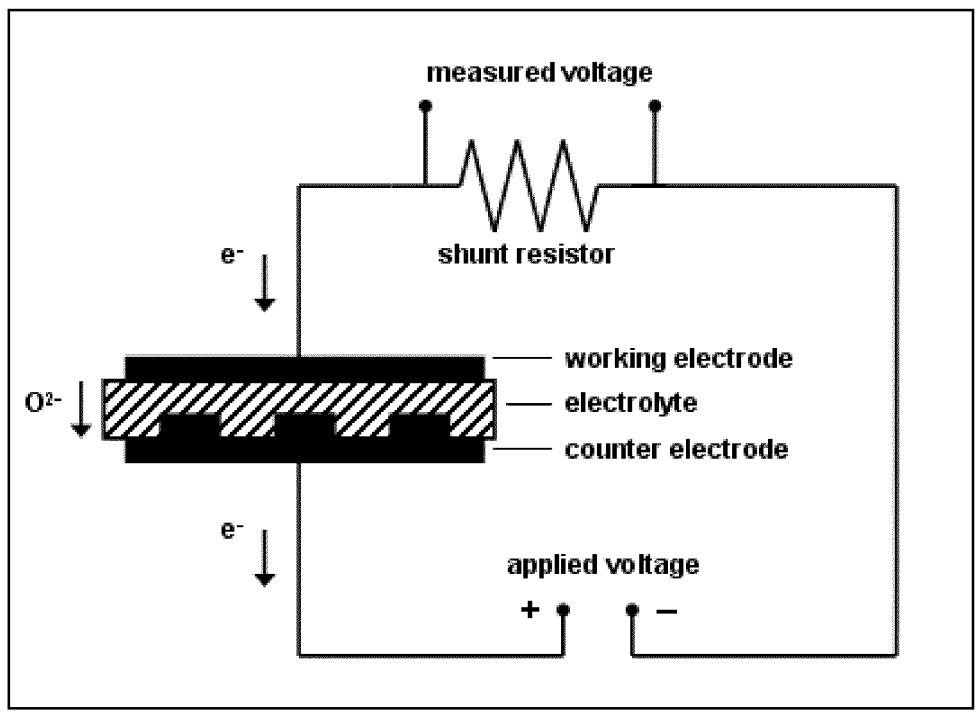
FIG. 2 is a schematic diagram of the test configuration used for testing $NO_X$ sensors of Examples 1 through 6.

For testing, the sensor is placed in a simulated fuel-lean diesel exhaust atmosphere, with temperature controlled over the approximate range of 200 to 550° C., and a constant voltage in the range of approximately 0.1 to 0.5 volts is applied to the cell. Voltage is measured across a shunt resistor, in series with the sensor, to determine the current passing through the cell, with various gases ($NO_X$, $NH_3$, and/or $SO_X$) being introduced into the simulated diesel exhaust atmosphere. The testing configuration is shown in FIG. 2.

Example 2

Demonstration of Sensing Mechanism

Figure 3:
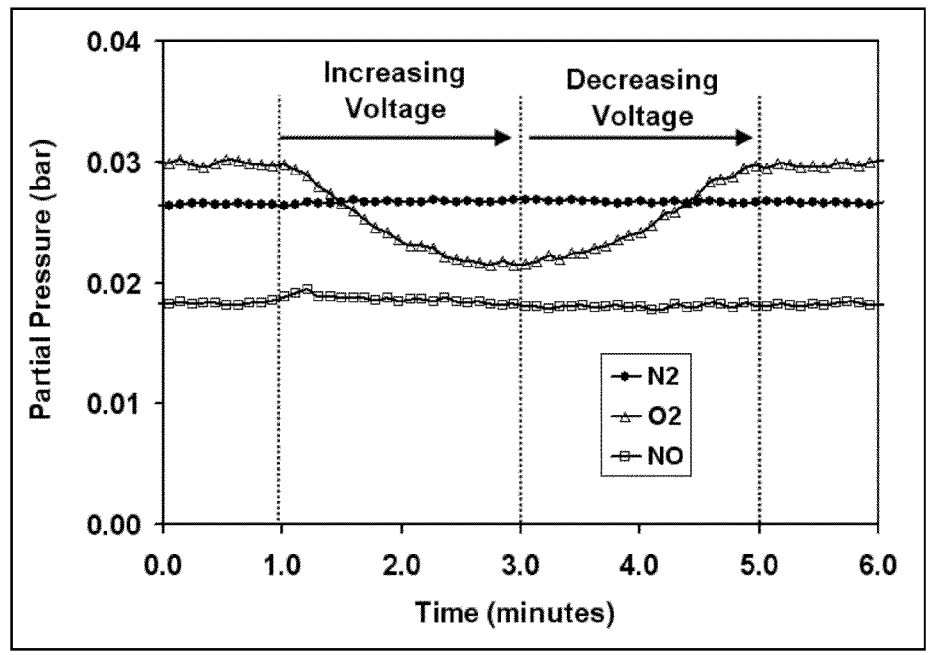
FIG. 3 is a graph showing the effect of varying applied voltage on the composition of the gas stream exiting the sensor chamber, as described in Example 2.

In this example, experiments were conducted to demonstrate the disclosed sensing mechanism of this invention. Specifically, experiments were designed to show that $NO_X$ is not reduced during the application of a voltage; only oxygen is reduced at the sensing electrode, the oxygen ions then being re-oxidized to molecular oxygen at the counter electrode. For these experiments, a sensor was fabricated as described in Example 1. The sample was loaded into a test chamber, such that the sensing and counter electrodes were sealed from one another, with the counter electrode being exposed to air, and the sensing electrode exposed to the gas stream being sensed. The gas composition was monitored downstream of the sensor to determine the effect of the electrochemical cell on the gas composition. During a sweep in the applied voltage, a corresponding drop in oxygen concentration was observed, indicating that oxygen was being pumped through the cell (see FIG. 3). The lack of change in nitric oxide composition indicates it was not being consumed in the process, but because the current is higher in the presence of $NO_X$, it is having a catalytic effect on oxygen reduction. It should be noted that the increase in current achieved in this test exceeds the amount possible through NO reduction to nitrogen, meaning the sensor has a higher response than an amperometric sensor based on $NO_X$ reduction.

Figure 4:
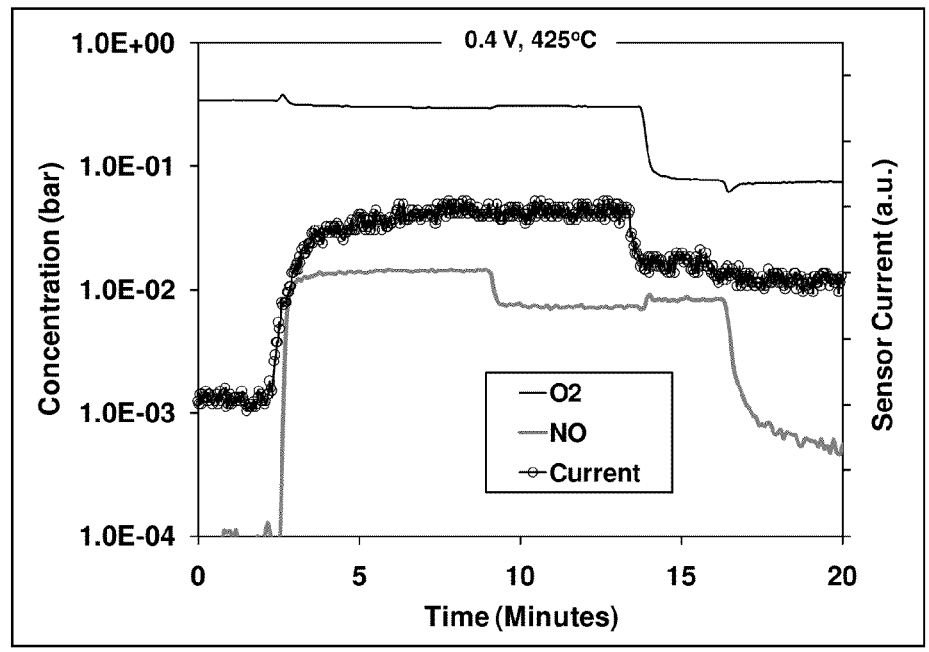
FIG. 4 is a graph showing the sensor response and a mass spectrum of gas species exiting the sensor chamber during an experiment showing the sensor dependence on adsorbed $NO_X$ without $CO_2$, as described in Example 2.
Figure 5:
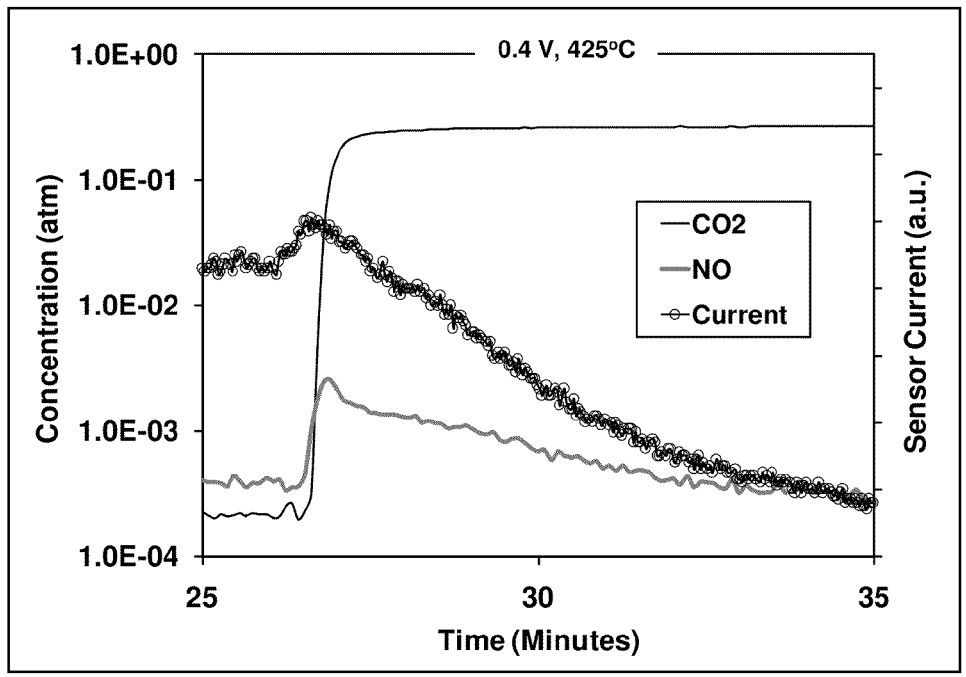
FIG. 5 is graph showing the sensor response and a mass spectrum of gas species exiting the sensor chamber during an experiment showing the sensor dependence on adsorbed $NO_X$ with $CO_2$ in the gas stream, as described in Example 2.

The catalytic effect of NO or $NO_2$ is present as long as $NO_X$ is adsorbed, as shown in FIG. 4 and FIG. 5. In FIG. 4, while the sensor is operating at an applied voltage of 0.4 volts, 100 ppm of NO is added to the gas stream, causing an increase in current. The current changes slightly when the oxygen level is adjusted, but is not dramatically affected when NO is removed. However, when carbon dioxide is added to the feed, NO is observed to desorb from the sensor, and the current drops (see FIG. 5). In an actual hydrocarbon combustion exhaust, $CO_2$ always will be present, allowing the sensor to recover quickly from an exposure to $NO_X$. Additionally, in an actual sensing environment, the sensing and counter electrodes do not need to be sealed from one another, and both electrodes could be exposed to the gas being sensed.

Example 3

Demonstration of Response Sensitivity to $NO_X$

Figure 6:
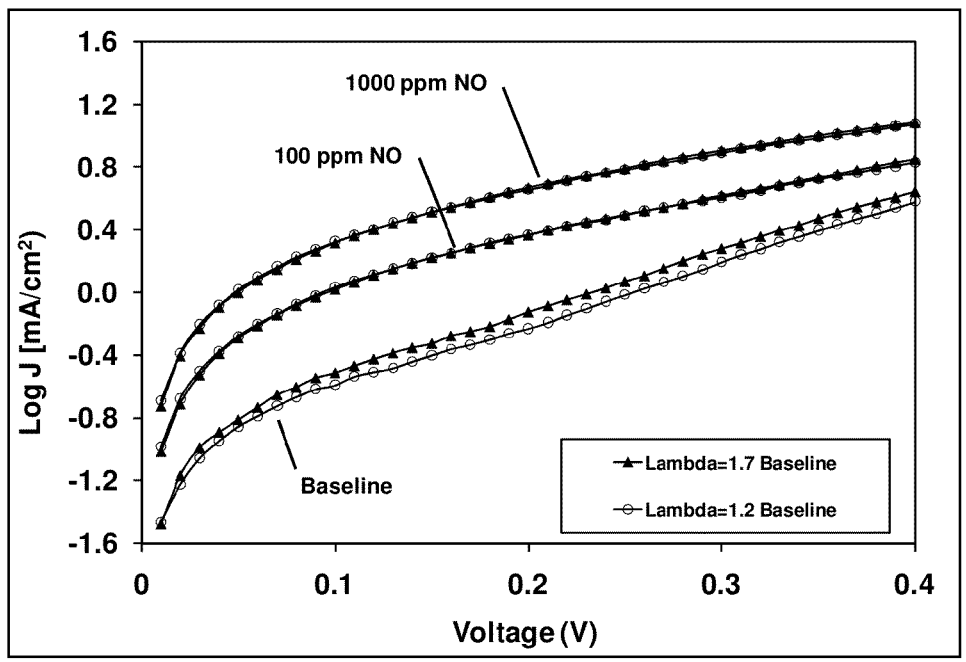
FIG. 6 is a graph with a comparison of Tafel plots, showing responses of a planar sensor with symmetrically opposed electrodes in different baseline gases at 425° C., as described in Example 3.
Figure 7:
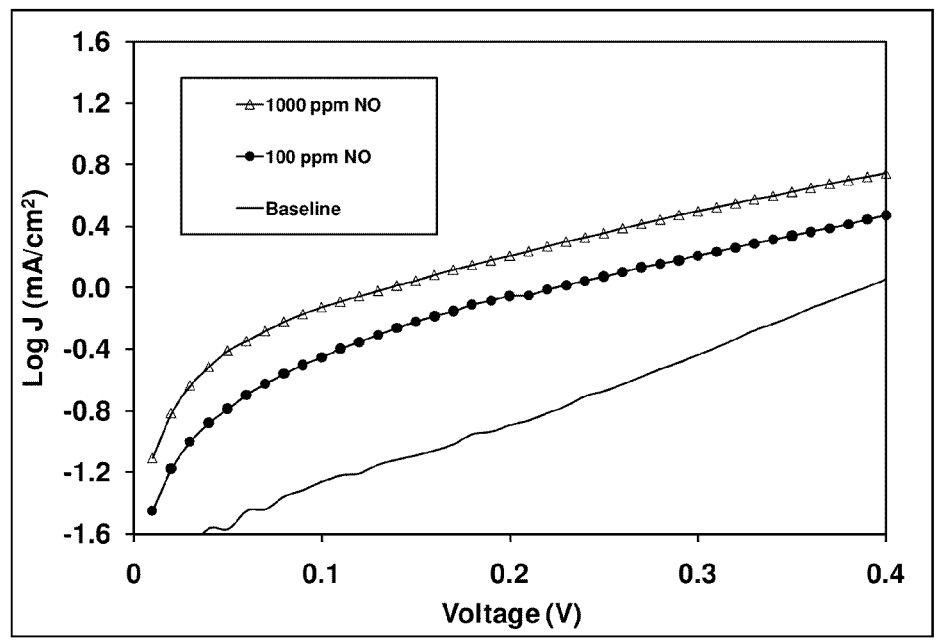
FIG. 7 is a graph with a comparison of Tafel plots, showing responses of planar sensors with symmetrically opposed electrodes to NO and $NH_3$ at 375° C. in a baseline gas composition of 3.3 vol % $O_2$, 11.3 vol % $CO_2$, 2 vol % $H_2O$ (balance $N_2$), as described in Example 3.

In this example, the response characteristics of the sensor to NO and $NO_2$ were evaluated, and experiments were conducted to demonstrate that the sensing mechanism is effective over a range of applied voltage, exhaust gas atmospheres, and temperatures, and is effective for NO and $NO_2$. A sensor was fabricated as described in Example 1. The sensor was then loaded into a test chamber such that both electrodes were exposed to the same gas environment. In this configuration, the responsiveness of the sensor at 425° C. to varying atmospheres at varying applied voltages is shown in FIG. 6, in the form of Tafel plots. Two different baseline gases were examined for these tests:
(1) the $\lambda=1.2$ gas contained 3.3 vol % $O_2$, 11.3 vol % $CO_2$, 2 vol % $H_2O$, the balance being an inert gas ($N_2$).
(2) the $\lambda=1.7$ gas contained 8.3 vol % $O_2$, 8.1 vol % $CO_2$, 2 vol % $H_2O$, the balance being an inert gas ($N_2$).
For each baseline gas, the effect of NO (100 and 1000 ppm), was examined. As can be observed in FIGS. 6 and 7, the presence of NO increases the oxygen reduction current over the range of applied voltages much more than the difference in current caused by changing the composition of the baseline gas. This holds true for tests conducted at approximately 550° C. and lower, although the baseline currents at about 200° C. become prohibitively low for accurate measurements.

Figure 8:
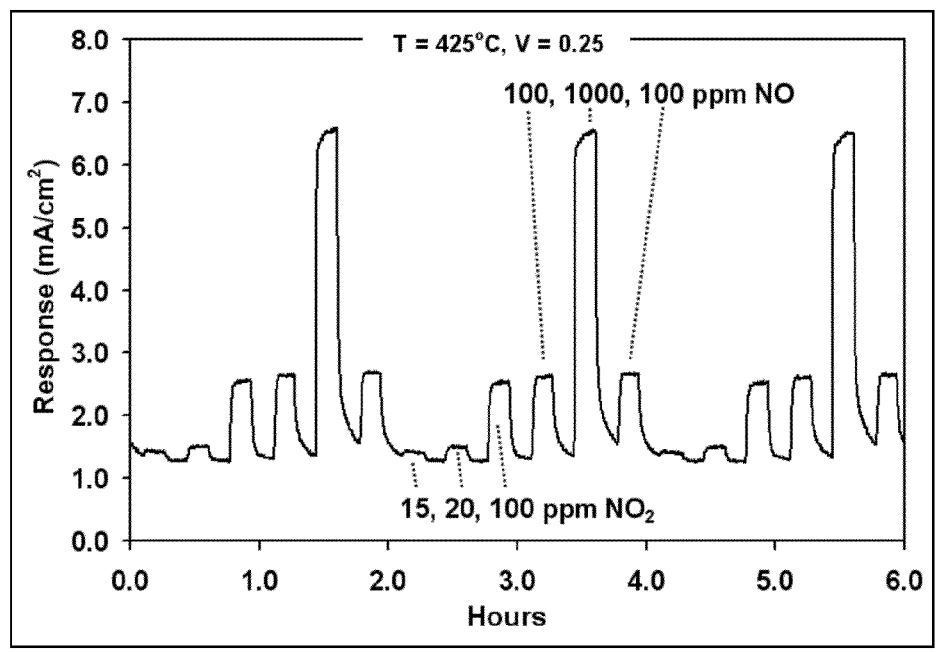
FIG. 8 is a graph showing the responses of a planar sensor with symmetrically opposed electrodes to $NO_2$ and NO at 425° C. in a baseline gas composition of 3.3 vol % $O_2$, 11.3 vol % $CO_2$, 2 vol % $H_2O$ (balance $N_2$), as described in Example 3.

Experiments were also conducted to quantify the relative sensitivity of the sensor to NO and $NO_2$. A sensor was fabricated as described in Example 1 and evaluated for its relative sensitivity to NO and $NO_2$. In this experiment, sensors were placed in a gas blending chamber through which simulated exhaust gas (baseline of 5 vol % $O_2$, 5% $CO_2$, 3 vol % $H_2O$, 10 ppm $NO_2$, balance $N_2$) was introduced at a constant flow rate of 200 sccm. NO and $NO_2$ test gases were each separately blended into the gas stream, and the resulting amperometric sensor output was measured in the previously described test configuration. As shown in FIG. 8, the response of the sensor is independent of whether $NO_X$ is in the form of NO or $NO_2$. In the presence of oxygen, it is likely that NO and $NO_2$ form interchangeably on the electrode surface. As FIG. 8 illustrates, the sensor displays equal sensitivity to NO and $NO_2$, compared at the 100 ppm NO and $NO_2$ peaks. This further supports the mechanism that the adsorbed NO and $NO_2$ on the sensor surface catalyze the oxygen reduction reaction. In contrast, sensor technologies based on reducing $NO_2$ and NO to $N_2$ and $O_2$ display sensitivity to $NO_2$ two times greater than to NO. FIG. 8 also shows the difference in sensor response from 15 ppm to 1000 ppm changes in $NO_X$ concentration, demonstrating the proportionality of the sensor response over this wide range.

Example 4

Demonstration of Effect of Promoter Addition to $NO_X$ Sensitivity

Figure 9:
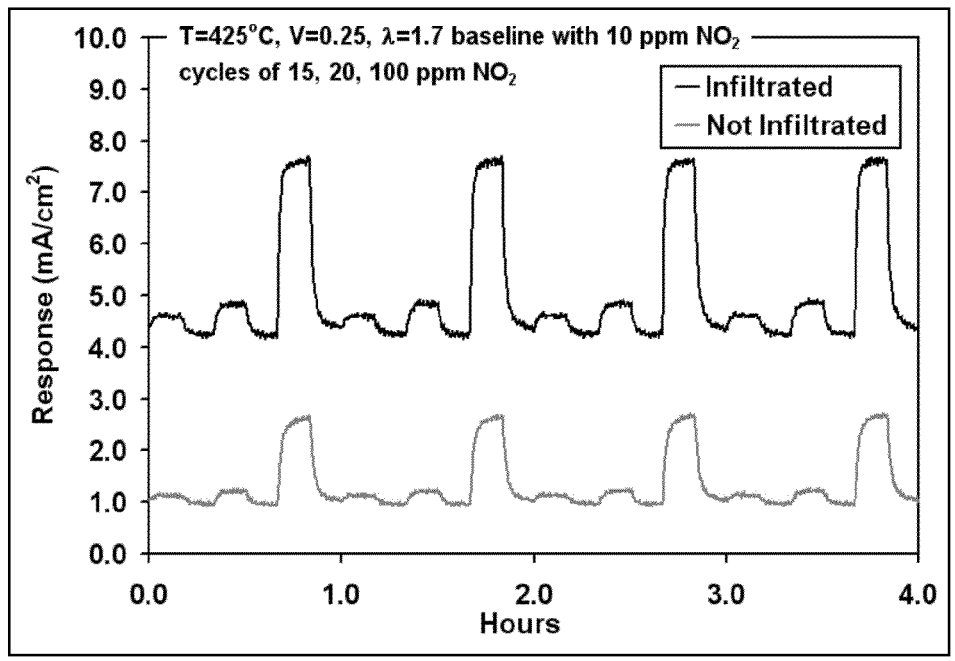
FIG. 9 is a graph showing the responses of planar sensors with symmetrically opposed electrodes at 425° C. made with and without GDC promoter additions to the sensing electrode, as described in Example 4.

In this example, the effect of the sensor response characteristics upon addition of a promoter to the electrode were examined. A sensor was fabricated as described in Example 1. The electrodes of the sensor were then infiltrated with an aqueous cerium nitrate solution using an incipient wetness approach. The infiltrated sensor was then dried and annealed, leaving a dispersed ceria phase within the electrode (approximately 5 percent of the electrode by weight). As shown in FIG. 9, the ceria-infiltrated sensor demonstrated higher current density and a larger response to $NO_2$ than a sensor without the infiltration when tested at 425° C. and 0.25 volts in a simulated exhaust stream. The infiltrated sensor, therefore, has the advantage of higher current per given electrode area, and a larger change in current during exposure to NOx, improving the corresponding signal strength for a given electrode area.

Example 5

Demonstration of Response Sensitivity to Ammonia

Figure 10:
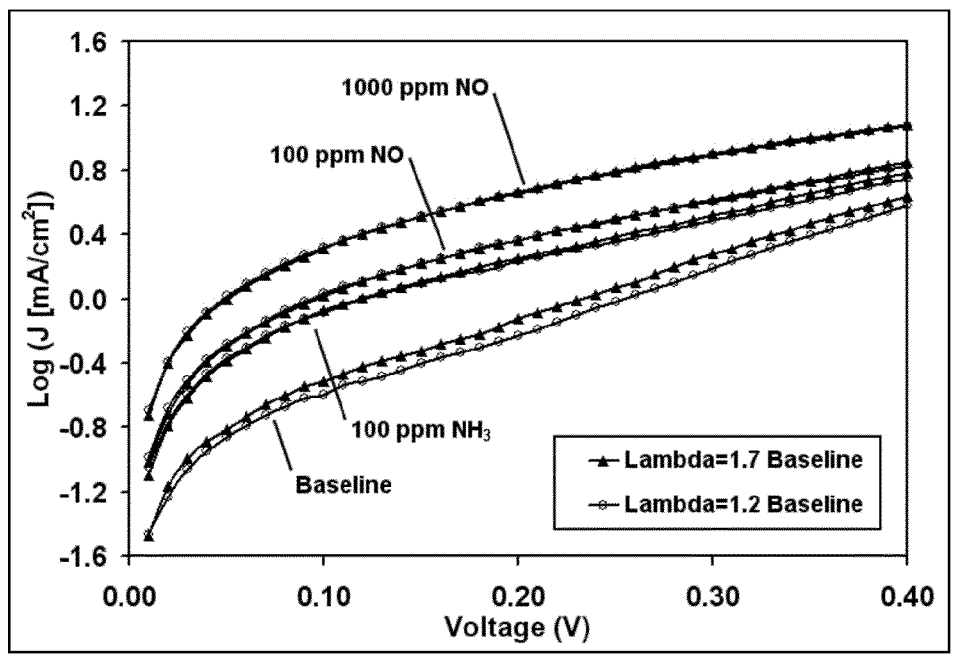
FIG. 10 is a graph with a comparison of Tafel plots, showing responses of planar sensors with symmetrically opposed electrodes in different baseline gases at 425° C., as described in Example 5.
Figure 11:
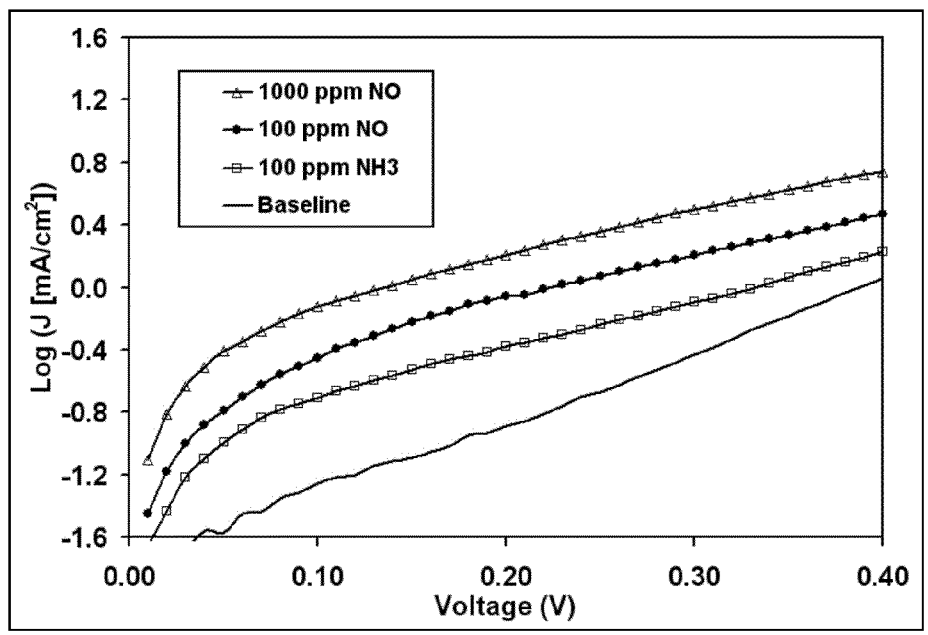
FIG. 11 is a graph with a comparison of Tafel plots showing responses of a planar sensor with symmetrically opposed electrodes to NO and $NH_3$ at 375° C. in baseline gas composition of 3.3 vol % $O_2$, 11.3 vol % $CO_2$, 2 vol % $H_2O$ (balance $N_2$), as described in Example 5.

In this example, the response characteristics of the sensor to ammonia were evaluated. A sensor was fabricated and tested, as described in Example 1. 100 ppm of ammonia was added to each of the background gas formulations, and the response was measured. FIG. 10 shows the responsiveness of the sensor at 425° C. to varying atmospheres at varying applied voltages, shown in the form of Tafel plots. As can be observed in FIG. 10, the presence of $NH_3$ increases the oxygen reduction current over the range of applied voltages much more than the difference in current caused by changing the baseline gas. This holds true for tests conducted at about 550° C. and lower, although the baseline currents at about 200° C. become prohibitively low for accurate measurements. A comparison to FIG. 11 shows that the relative response of the sensor to $NO_X$ and $NH_3$ is dependent on the voltage and the temperature of operation. At lower temperatures and higher voltages, the $NO_X$ response becomes greater than the ammonia response at equivalent conditions. Therefore, by employing multiple sensors at different temperatures and/or voltages, or alternating the voltage of a single sensor, a combined $NO_X$ and ammonia sensor could be envisioned.

Figure 12:
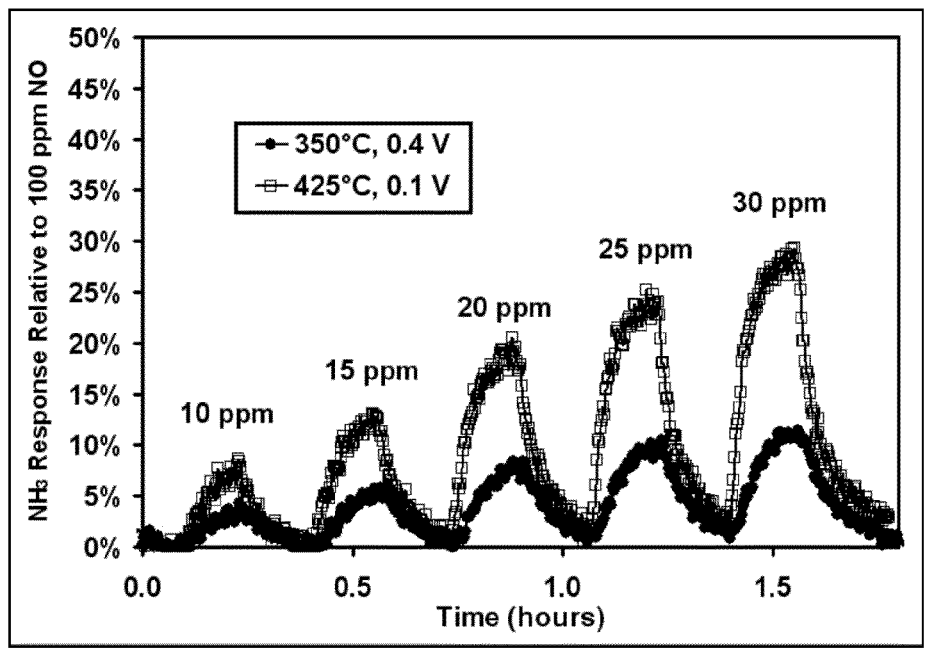
FIG. 12 is a graph showing the relative response of a planar $NO_X$ sensor with symmetrically opposed electrodes to $NH_3$ (relative to 100 ppm NO) in a baseline gas composition of 5 vol % $O_2$ and 5 vol % $CO_2$ (balance $N_2$), as described in Example 5.

This concept is illustrated in FIG. 12. In this experiment, $NH_3$ was introduced in concentrations ranging from 0 to 30 ppm. The sensor exhibited a strong cross-sensitivity to ammonia under higher temperature and lower applied voltage conditions (425° C., 0.1 volts), but displayed significantly lower sensitivity at lower temperature and higher applied voltage conditions (350° C., 0.4 volts). At 30 ppm, the ammonia sensitivity was almost 30 percent of the response to 100 ppm NO at the 425° C. condition; however, the response dropped to only 11 percent at the 350° C. condition. By manipulating these operating conditions through the sensor's electronics controller, this variable sensitivity to ammonia with respect to the $NO_X$ response could enable both the $NO_X$ and $NH_3$ concentrations to be determined in a single sensor.

Example 6

Demonstration of $NO_X$ the of $SO_X$

Figure 13:
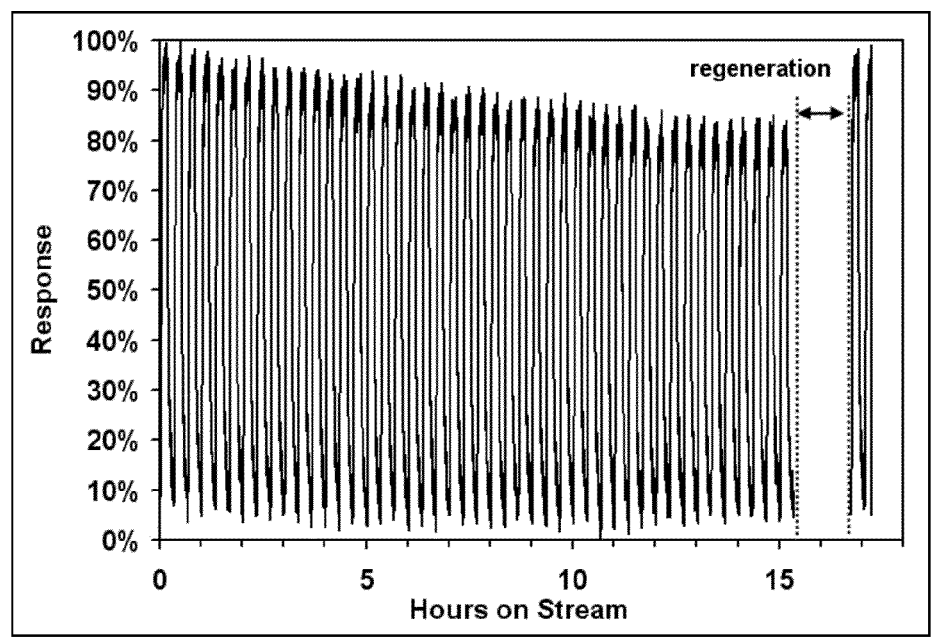
FIG. 13 is a graph showing the operation of a planar sensor with symmetrically opposed electrodes during cycles of 100 ppm NO in baseline gas composition of 3.3 vol % $O_2$, 11.3 vol % $CO_2$, 2 vol % $H_2O$, 1 ppm $SO_2$, (balance $N_2$) at 350° C. and 0.1 volts, as described in Example 6. After 15 hours, sensor was regenerated by heat treatment at 800° C.

In the targeted diesel exhaust application, a $NO_X$ sensor may be exposed to a range of $SO_X$ levels, continuously or intermittently. In this example, the sensitivity of the sensor to $SO_X$ was evaluated. Sensors were fabricated as describe in Example 1 and tested for sensitivity to $SO_X$ by injecting 1 ppm $SO_2$ into a simulated exhaust stream. As FIG. 13 shows, 20 percent degradation in responsiveness was observed over 15 hours; however, by increasing the temperature to 800° C., complete reversal of this degradation was observed. This allows the electronics of the sensor device to be designed with a periodic excursion to an elevated temperature as a means of mitigating the effect of $SO_2$ on the sensor response. In the ideal configuration, this excursion would not require heating a furnace, and could therefore take place much faster.

Example 7

Demonstration of Response Time

Figure 14:
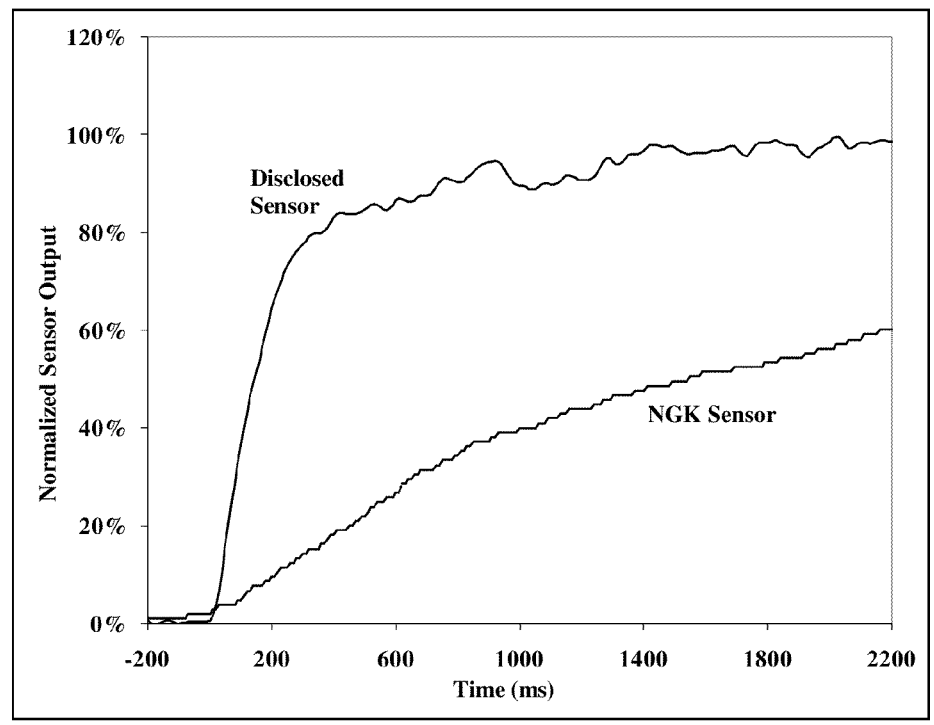
FIG. 14 is a graph showing the response of a planar sensor with symmetrically opposed electrodes to step changes in $NO_X$ concentration from 0 to 100 ppm at 400° C., with 0.25 volts applied to the sensor, and with a background oxygen level of 16 percent $O_2$ in a slip stream of a gasoline engine exhaust, compared to response of a commercial $NO_X$ sensor manufactured by NGK Insulators, as described in Example 7.

In this example, the response time of the sensor to detect NOx was evaluated in the exhaust stream of a gasoline engine dynamometer. A sensor was fabricated as described in Example 1, and then clamped between steel washers and mounted in a slip stream of the post three-way catalyst exhaust, equipped with a gas heater to elevate the exhaust gas temperature to 400 to 450° C. The engine was stabilized at exhaust conditions containing 8.9 percent $O_2$ and 8.7 percent $CO_2$. NO and $NO_2$ were injected from bottled gas cylinders directly into the exhaust stream, just upstream of the sensor at concentrations ranging from 1 to 100 ppm. As shown in FIG. 14, response times of approximately 180 mS were observed, determined as time to reach 60 percent of the sensor's stabilized output. A commercial $NO_X$ sensor, manufactured by NGK Insulators, was tested in the same manner, and the response of this sensor also is shown in FIG. 14. The response time of the NGK sensor was on the order of 2-3 seconds, an order of magnitude slower than the disclosed sensor. Further, the response time of the disclosed sensor is much faster than other amperometric and potentiometric technologies reported in the literature.

Example 8

Planar Sensor with Electrodes Printed on Same Side of GDC Electrolyte

Figure 15:
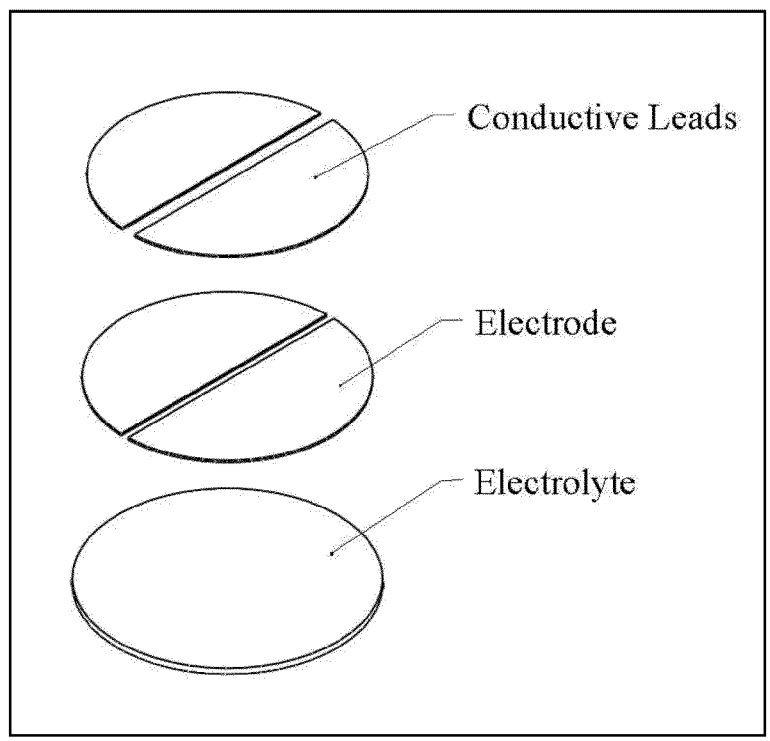
FIG. 15 is a drawing of a sensor with both electrodes printed on the same side of a GDC substrate, as described in Example 8.
Figure 16:
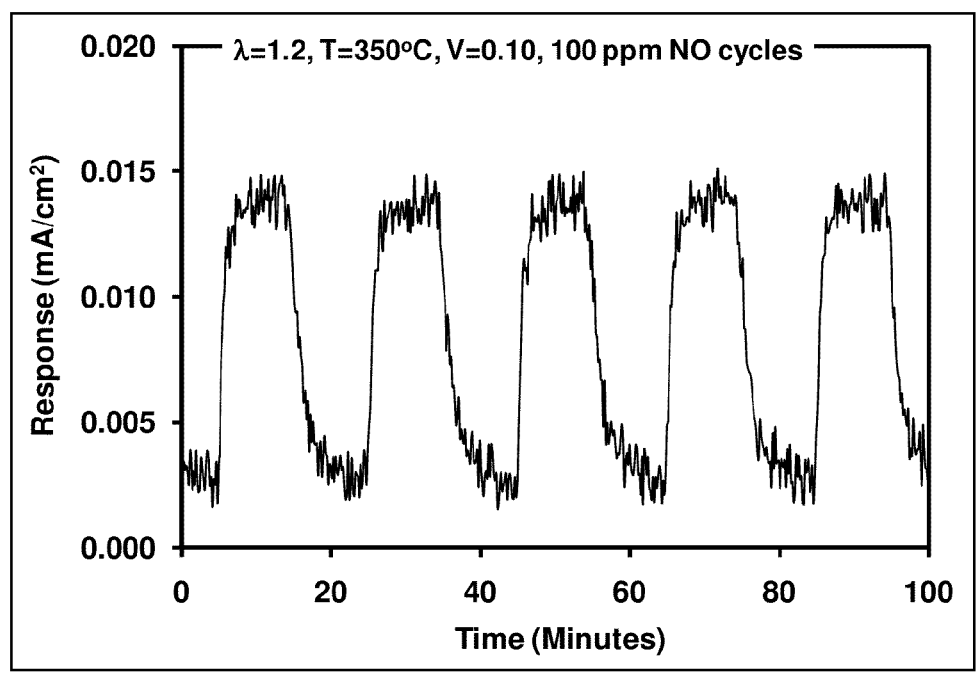
FIG. 16 is a graph showing the responses of a same-plane electrode sensor to 100 ppm NO at 350° C., as described in Example 8.

For improved manufacturability, sensors were built with both electrodes printed on one face of the electrolyte substrate. In this example, two LSCF electrodes were printed onto one face of a GDC ceramic electrolyte disc having a thickness of approximately 0.3 mm. As shown in FIG. 15, the substrates were semicircular in shape with a gap between them of approximately 0.3 mm. Gold was then printed on top of the LSCF electrode pattern to facilitate current collection. For testing, the sensor was placed in a simulated fuel lean diesel exhaust atmosphere, heated to 350° C. with furnace heat, and a constant voltage of approximately 0.1 volts was applied to the cell. Voltage was measured across a 100 ohm shunt resistor, in series with the sensor, to determine the current passing through the cell. The response of this sensor configuration is shown in FIG. 16, showing a repeatable step change response to 100 ppm NO.

Example 9

Same Plane, Interdigitated Electrode Configuration, Thick Film of GDC

Figure 17:
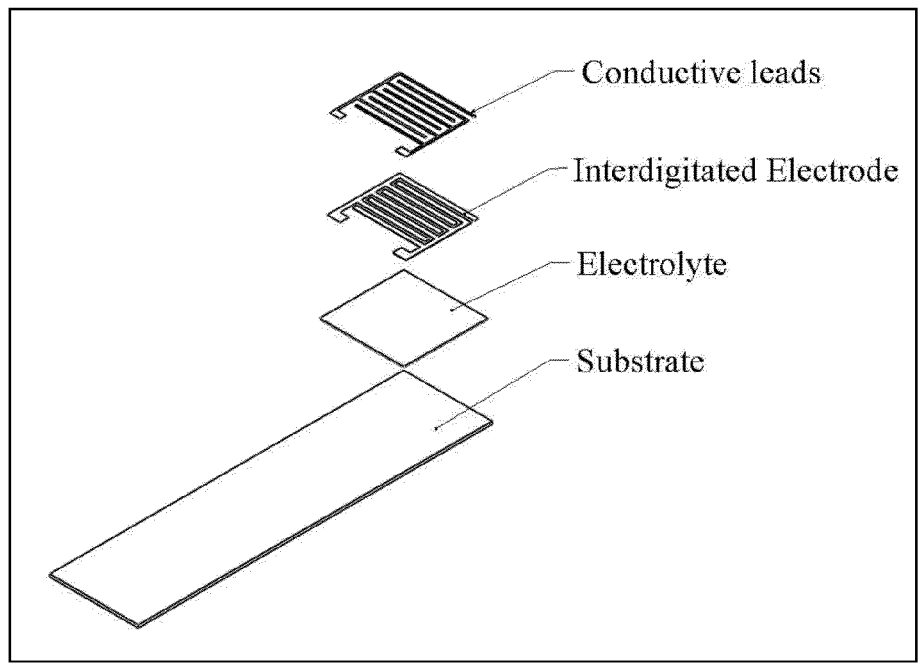
FIG. 17 is a drawing showing a same-plane electrode sensor made with interdigitated electrodes deposited on a thick-film of a GDC electrolyte membrane, as described in Example 9.
Figure 18:
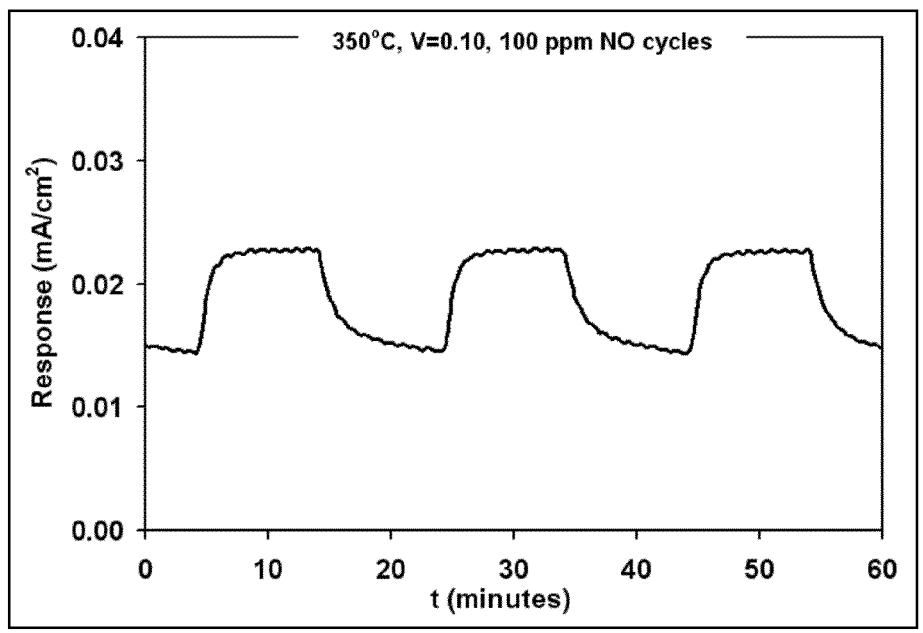
FIG. 18 is a graph showing the response of a same-plane electrode sensor made with interdigitated electrodes deposited on a thick-film of a GDC electrolyte membrane to repeated exposures to 100 ppm NO, with 0.1 volts applied across the sensor electrodes as described in Example 9.

In this example, further design modifications were made over Example 8 to improve the manufacturability of the sensor design. In this example, a thick film (~0.050 mm thick) of GDC was printed onto an yttrium stabilized zirconia (8 mol % $Y_2O_3$ or YSZ) substrate (approximately 0.150 mm thick) and sintered to densify the GDC electrolyte film. LSCF electrodes were printed on top of the GDC thick film in an interdigitated electrode pattern, as shown in FIG. 17. Gold was then printed on top of the LSCF electrode pattern to facilitate current collection. For testing, the sensor was placed in a simulated fuel-lean diesel exhaust atmosphere, heated to 350° C. with furnace heat, and a constant potential of approximately 0.1 volts was applied to the cell. Voltage was measured across a shunt resistor, in series with the sensor, to determine the current passing through the cell. The response of this sensor configuration is shown in FIG. 18, showing a repeatable step change response to 100 ppm NO.

Example 10

Interdigitated Electrode Configuration with Integrated Heater

Figure 19:
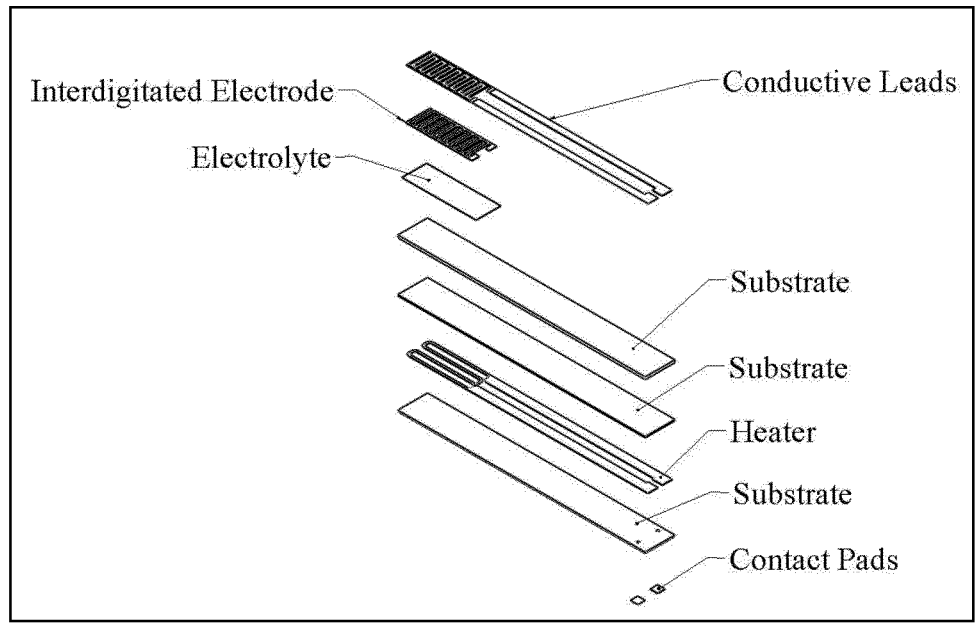
FIG. 19 is a drawing showing an exploded view of a same-plane electrode sensor design, made with interdigitated electrodes deposited on a thick-film of GDC electrolyte membrane as described in Example 10. The design also includes a heater component to elevate the sensor temperatures to the target operating range of 200 to 550° C.

In this example, further modifications were made to the sensor design over Example 9, for ease of use in an exhaust environment (FIG. 19). In this design, a thick film of GDC is applied, over a length of approximately 10 to 15 mm from, the end of a YSZ substrate of nominal dimensions of 6 mm wide by 50 mm long. LSCF electrodes are applied in an interdigitated electrode pattern over the GDC print, and gold is applied in the same IDE pattern to carry the signal back to the data acquisition system. A separate heater is attached to this sensing element to enable the sensor temperature to be controlled to the target operating temperature. The resistive heater is made from Pt or other precious metal alloy and is applied to an aluminum oxide substrate of the same nominal dimensions as the YSZ component. The heater is attached to the YSZ component with a high temperature ceramic adhesive. Alternatively, the YSZ layers could be replaced with aluminum oxide, allowing the sensor and heater components to be one monolithic component. An optional porous protective coating could be applied to protect active sensing region from particulate matter.

Example 11

Sensor Packaging for Symmetrically Electroded Planar Sensor Elements

Figure 20:
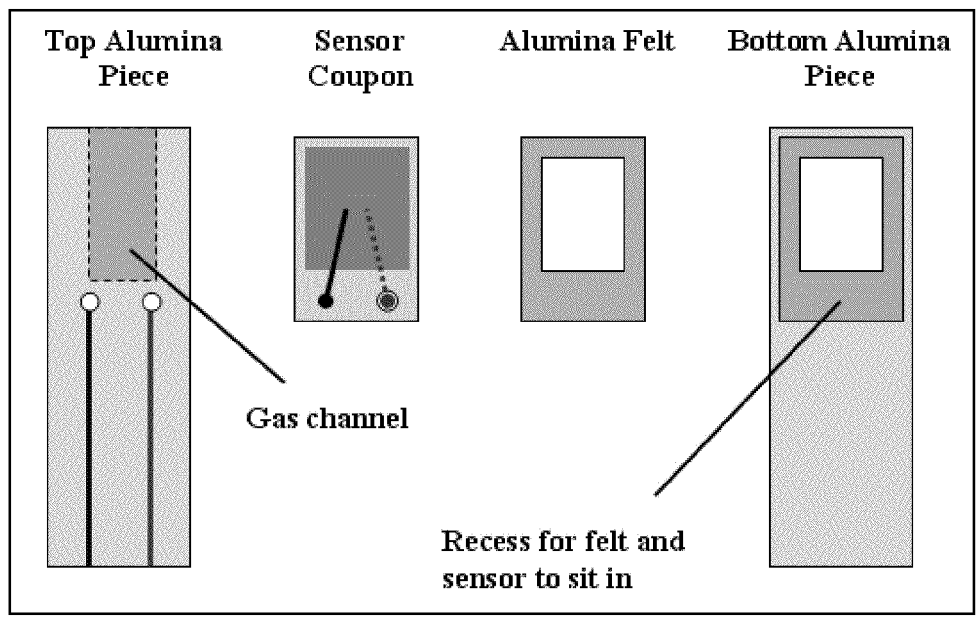
FIG. 20 is a diagram of the parts required for assembly of an integrated sensor that utilizes a planar sensor element with symmetrically opposed electrodes, as described in Example 1.

This example describes a packaging approach for utilizing symmetrically electroded sensing elements fabricated as described in Example 1. A drawing of the packaging design is shown in FIG. 20. Four pieces are required for assembly of the sensor. Two pieces of alumina serve as the housing for the sensor coupon. The bottom piece contains a hole for exposure to the sensing gas, and a recess in which a piece of alumina felt is placed. The felt is a compliant material that prevents the sensor from being crushed when the alumina pieces are adhered to one another. The sensor coupon is then placed on the alumina felt. The coupon consists of a solid planar ceria electrolyte with electrodes on each side. Metallic (e.g., gold or platinum) pads are painted on each electrode, with the pad on the bottom of the sensor leading to a hole in the electrolyte. The hole is filled with metallic ink to establish contact of the bottom electrode to the same side of the coupon as the top electrode. The top alumina piece is attached to the bottom piece with a bonding agent, such as ceramic cement that binds alumina to alumina (see FIG. 21 for placement of bonding agent). The top piece contains a channel (or hole) that allows oxygen being pumped to that electrode to escape. The electrical pads may be painted on the top or bottom of the top alumina piece. If painted on the top, as in FIG. 20, then the top piece would require holes that would be filled with metallic ink. In this configuration, the coupon would be mechanically attached to the top alumina piece via the electrical leads. This would have the advantage of preventing the sensor to move around within the recess, but the disadvantage would be that the leads could break at this joint, and electrical contact would be lost.

Figure 21:
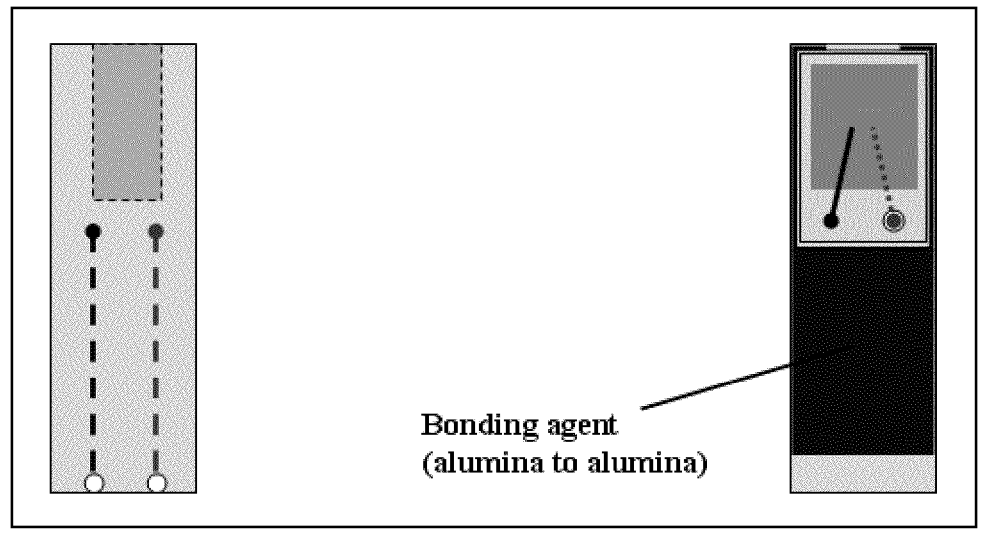
FIG. 21 is a diagram of a nearly assembled integrated sensor that utilizes a planar sensor element with symmetrically opposed electrodes, as described in Example 1.

In the configuration shown in FIG. 21, the leads are placed on the bottom of the top alumina piece. With this configuration the leads on the coupon and the leads on the alumina are electrically connected, but not mechanically connected. The advantage of this approach is that there is no mechanical joint to break and loose contact, the spring constant of the felt keeps the two contacts connected. However, this approach has the disadvantages in the fact that the coupon could slide around more and possible break, or vibrations may cause a loss of electrical connection momentarily (or over time if the felt spring constant changes).

In either configuration, a heater would be placed on one or both faces of the sensor. A symmetrical assembly could also be envisions were a second sensor assembly is placed on the opposite side of the heater. This could allow for doubling the sensor output or for detection of alternative species, such as ammonia. The sensor(s) would be placed within a shield for further protection. The bottom of the sensor would extend out of the shield and lead to the electrical connections. A sealant at the bottom would bond the sensor element to the shield and keep exhaust gases from escaping, as is done in commercial oxygen sensors.

Example 12

Figure 22:
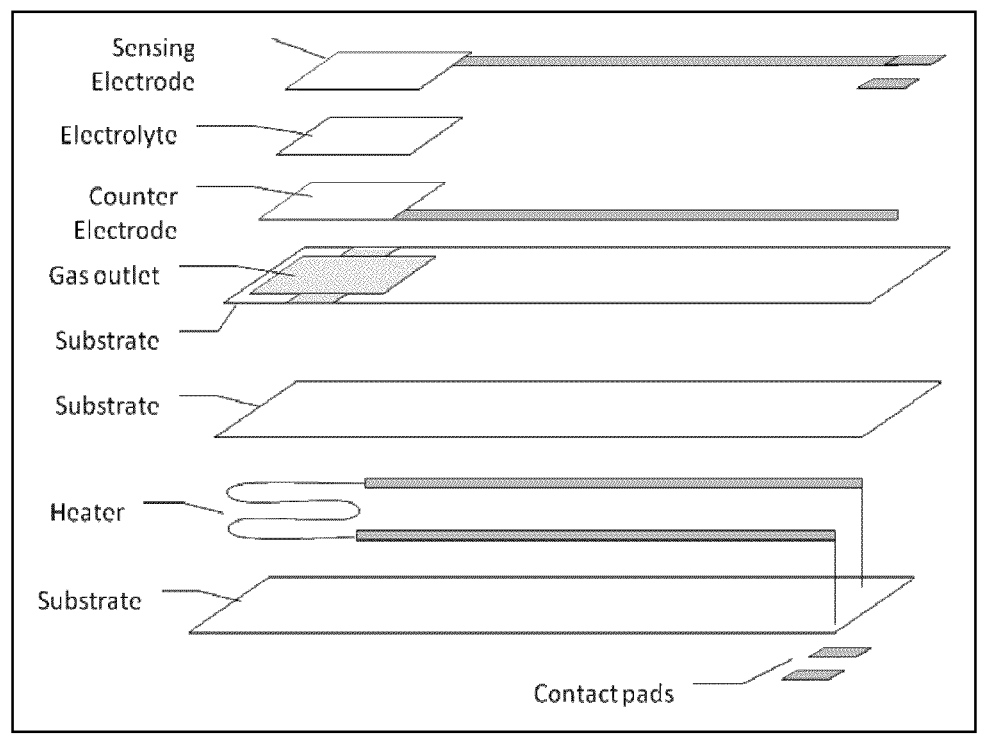
FIG. 22 is a drawing of a sensor design with electrodes printed on opposite sides of a thick film of electrolyte, as described in Example 12. The design also includes a heater component to elevate the sensor temperatures to the target operating range of 200 to 550° C.

Sensor with Electrodes Deposited on Opposite Sides of Thick Film Electrolyte Layer In this example, an alternative sensor configuration was designed to with electrodes printed on opposite sides of a thick film GDC electrolyte layer (FIG. 22). In this design, the counter electrode is deposited onto a YSZ substrate of nominal dimensions of 6 mm wide by 50 mm long. A thick film of GDC (approximately 0.20 to 0.50 mm) is applied over the counter electrode. An LSCF sensing electrode is applied over the GDC print, and gold is applied over the LSCF to carry the signal back to the data acquisition system. With this configuration, the separation between electrodes (dictated by the thickness of the GDC layer) is minimized compared to the interdigitated electrode approach of Example 10, in which case the spacing between electrodes is limited by the capability of manufacturing methods such as screen or ink jet printing of electrode inks. A porous or fugitive gas outlet is included directly under the counter electrode to allow the recombined oxygen gas molecules to exit the sensor from the counter electrode. Alternatively, the electrolyte layer or counter electrode could be designed with sufficient porosity to allow for venting of the oxygen, thus eliminating the need for the gas outlet.

A separate heater is attached to this sensing element to enable the sensor temperature to be controlled to the target operating temperature. The resistive heater is made from Pt or other precious metal alloy and is applied to an aluminum oxide substrate of the same nominal dimensions as the YSZ component. The heater is attached to the YSZ component with a high temperature ceramic adhesive. Alternatively, the YSZ layers could be replaced with aluminum oxide, allowing the sensor and heater components to be one monolithic component. An optional porous protective coating could be applied to protect active sensing region from particulate matter.

Example 13

Figure 23:
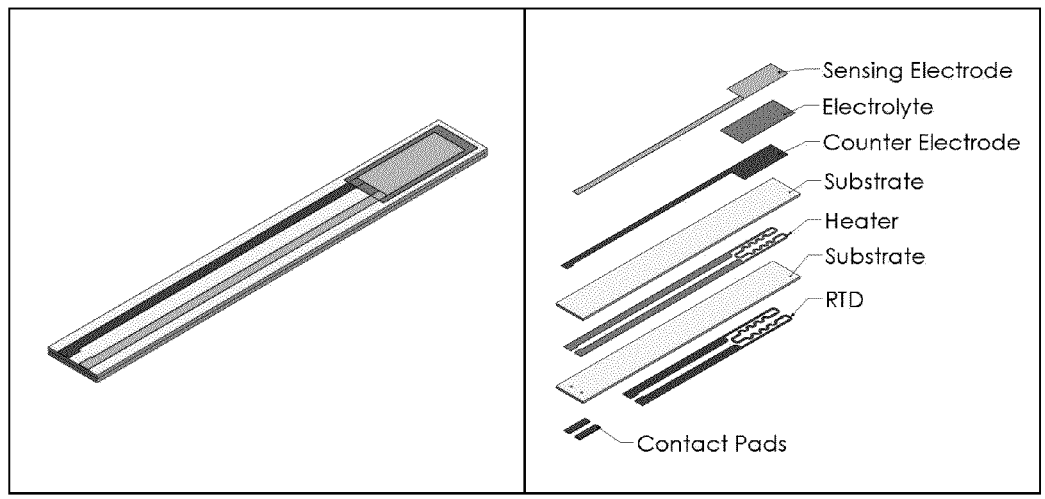
FIG. 23 is a drawing of an alternative sensor design with electrodes printed on opposite sides of a thick film of electrolyte on an aluminum oxide substrate, as described in Example 13. The design includes a heater that is embedded within the substrate to elevate the sensor temperatures to the target operating range of 200 to 550° C.

Simplified Sensor made with Electrodes Deposited on Opposite Sides of Thick Film Electrolyte Layer In this example, the sensor configuration of Example 12 is further simplified by eliminating some of the layers and combining others (see FIG. 23). The substrate comprises aluminum oxide (instead of YSZ), with an embedded platinum heater and a platinum counter electrode on one face of the substrate. The substrate is fabricated from two green sheets (or tapes) of aluminum oxide (made by tape casting of $Al_2O_3$ powder). A patterned platinum heater is screen printed onto the first green alumina tape layer, and a counter electrode is screen printed onto the second green alumina tape layer. The two green tape layers then are laminated together by applying pressure at slightly elevated temperature (at or slightly above the softening temperature of the polymeric binders used during tape casting of the alumina layers). The multilayer substrate is completed by heating the component to a temperature of 400 to 600° C. at which organic binders are volatilized, and then further heating the component to a higher temperature of 1400 to 1600° C., where the planar multilayer substrate sinters to high density. A GDC coating is then applied on top of the platinum counter electrode, and sintered at a temperature of 1200 to 1400° C. so that the coating densifies and adheres to the counter electrode. The thickness of the GDC electrolyte layer can range from approximately 20 to 200 microns. The GDC electrolyte coating may be formed as a porous material to allow venting of oxygen gas that is evolved during sensor operation. Fabrication of the sensor is completed by depositing a sensing electrode made of LSCF or other electrode materials that are sensitive to the presence of nitrogen oxides. Optionally, a platinum RTD pattern can be deposited on the aluminum oxide substrate face on the opposite side of the GDC and sensing electrode coatings to provide a temperature measurement means.

Example 14

Demonstration of Alternative Electrode Composition

This example describes a variation in the electrode composition that exhibits response to nitrogen oxides. A sensor was prepared in the same configuration and procedure to that described in Example 9. However, instead of printing LSCF electrodes on the sensor, a composite of 50 wt % of $(La_{0.06}Sr_{0.40})(Zn_{0.10}Fe_{0.90})O_{3-\delta}$ (LSZF) and 50 wt % of GDC, with a 1-wt % addition of palladium as a promoter, was printed onto the GDC film in an interdigitized pattern. Gold leads were printed on the electrodes. For testing, the sensor was placed in a simulated fuel-lean diesel exhaust atmosphere, heated to 350° C. with furnace heat, and a constant potential of approximately 0.1 volts was applied to the cell. Voltage was measured across a shunt resistor, in series with the sensor, to determine the current passing through the cell. The response of this sensor composition is shown in FIG. 23, showing a repeatable step change response to 100 ppm NO.

Example 15

Demonstration of Alternative Electrode Composition

This example describes yet another variation in the electrode composition that exhibits response to nitrogen oxides. A sensor was prepared in the same configuration and using the same procedure as described in Example 13. The thickness of the porous GDC electrolyte film was 45 microns. However, instead of printing LSCF electrodes on the sensor, a composite of 50 vol % of platinum and 50 vol % of GDC was printed onto the GDC film.

Figure 24:
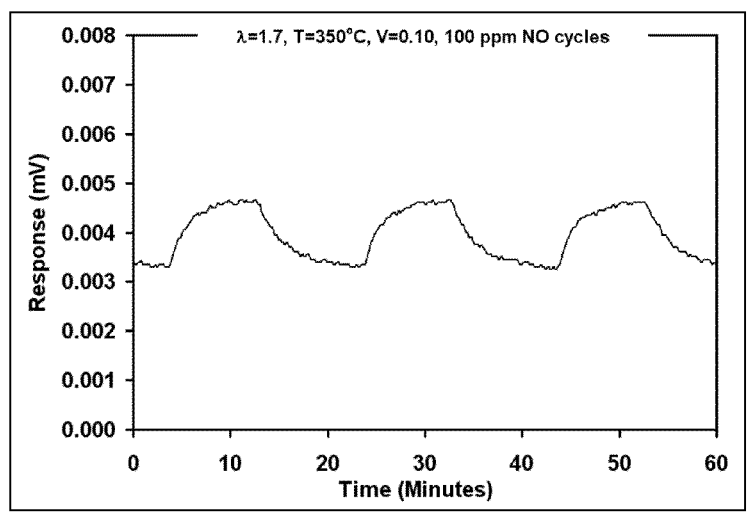
FIG. 24 is a graph showing the response of a sensor made with a platinum counter electrode and a Pd-doped LSZF sensing electrode on opposite faces of a thick-film of a GDC electrolyte membrane that is deposited on an aluminum oxide substrate to repeated exposures to 100 ppm NO, with 0.1 volts applied across the sensor electrodes as described in Example 14.
Figure 25:
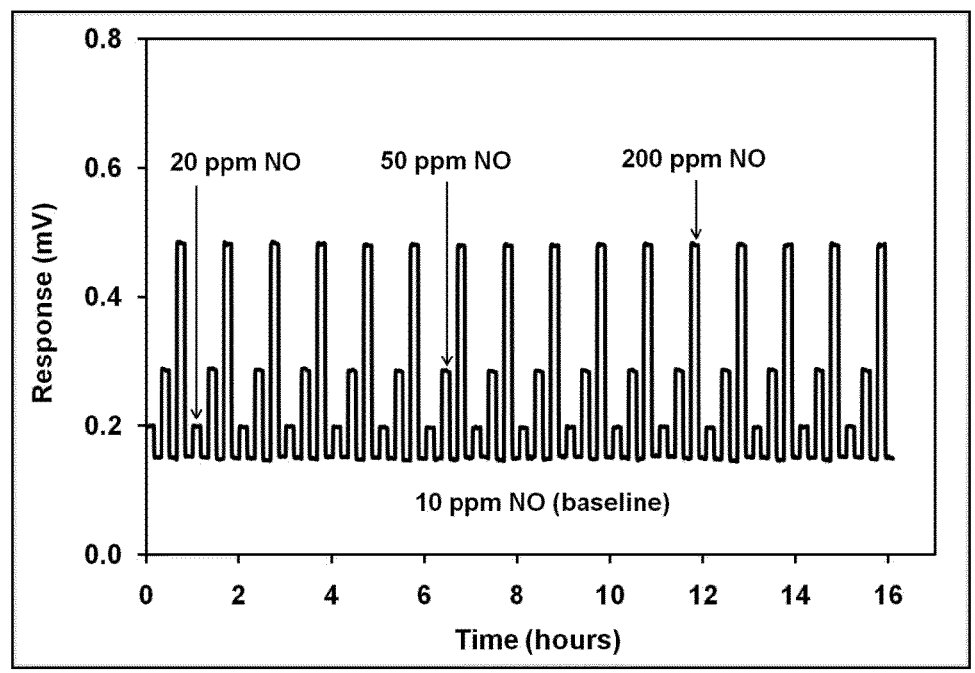
FIG. 25 is a graph showing the response of a sensor made with a platinum counter electrode and a Pt/GDC cermet sensing electrode on opposite faces of a thick film of a GDC electrolyte membrane that is deposited onto an aluminum oxide substrate during cycled exposures of 10, 20, 50 and 200 ppm NO in simulated combustion exhaust (8% $O_2$, 8% $CO_2$) at 375° C., with 0.1 volts applied across the sensor electrodes, as described in Example 15.
Figure 26:
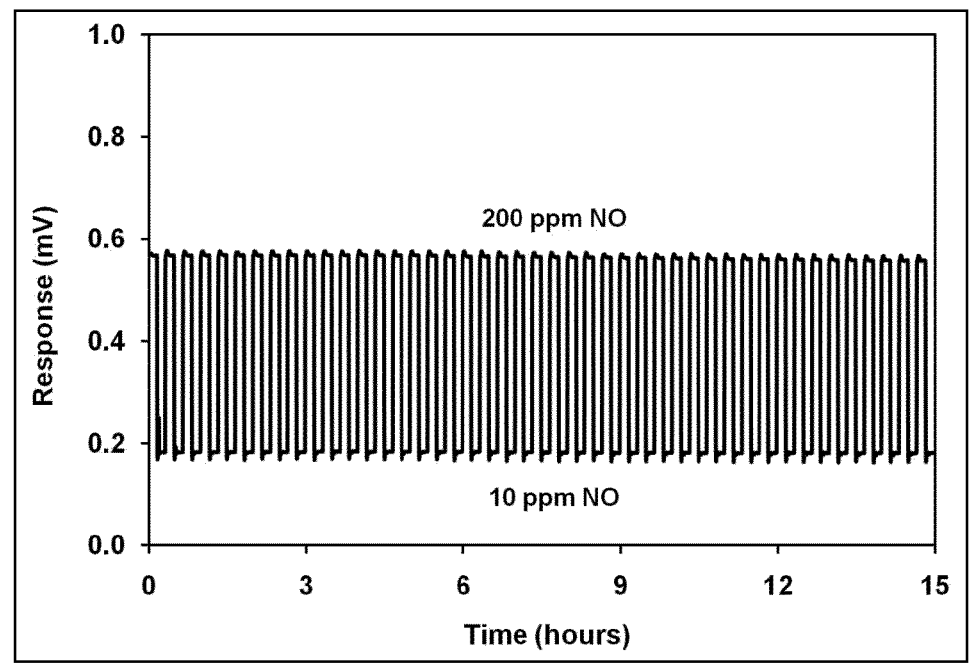
FIG. 26 is a graph showing the response of a sensor made with a platinum counter electrode and a Pt/GDC cermet sensing electrode on opposite faces of a thick film of a GDC electrolyte membrane that is deposited onto an aluminum oxide substrate during cycling between 10 and 200 ppm NO in simulated combustion exhaust (8% $O_2$, 8% $CO_2$) containing 1 ppm $SO_2$ at 375° C., with 0.1 volts applied across the sensor electrodes, as described in Example 15.

Gold lead wires were attached to the Pt counter electrode and the Pt/GDC sensing electrodes. For testing, the sensor was placed in a simulated fuel-lean diesel exhaust atmosphere, heated to 375° C. with furnace heat, and a constant potential of approximately 0.1 volts was applied to the cell. Voltage was measured across a shunt resistor, in series with the sensor, to determine the current passing through the cell. The response of this sensor composition is shown in FIG. 23. FIG. 23 shows quantitative and repeatable step change responses to 10, 20, 50 and 100 ppm NO. The sensor also provided relatively stable responses during cycling between 10 and 100 ppm NO in the presence of 1 ppm $SO_2$ as shown in FIG. 24, as compared to similar data obtained for a sensor of Example 6 made with an LSCF electrode (shown previously in FIG. 13)

The specific illustrations and embodiments described herein are exemplary only in nature and are not intended to be limiting of the invention defined by the claims. Further embodiments and examples, and the advantages thereof, will be apparent to one of ordinary skill in the art in view of this specification and are within the scope of the claimed invention.

What is claimed:

1. A method for amperometrically detecting the concentration of one or more nitrogen oxides (NOX) and/or ammonia (NH3) in a gaseous oxidizing atmosphere, comprising:
    exposing an amperometric sensor to the gaseous atmosphere, wherein the sensor includes
        an ionically-conductive, porous electrolyte layer, said porous electrolyte comprising cerium oxide doped with Ca, Sr, Sc, Y, Pr, Nd, Pm, Sm, Eu, Gd, Tb, Dy, Ho, Er, Tm, Yb, La, or a mixture thereof, said porous electrolyte having sufficient porosity such that oxygen is vented from the sensor through the electrolyte,
        a sensing electrode layer comprising a continuous network of a ceramic phase and a metallic phase, and
        a counter electrode layer,
    wherein the sensing and counter electrode layers are positioned on opposite sides of the porous electrolyte, and the sensing electrode layer is exposed to the gaseous atmosphere, and further wherein the ceramic phase of the sensing electrode layer comprises Gd or Sm-doped ceria, and the metallic phase of the sensing electrode layer comprises Pt, Pd, or an alloy or mixture thereof;
    applying a voltage bias between the sensing electrode and counter electrode layers of about 0.1 to about 1 volt, such that oxygen ion current flows through a thickness of the porous electrolyte layer and the oxygen ions are oxidized to oxygen gas at the counter electrode;
    measuring the resulting current through the sensor, wherein the oxygen gas from the counter electrode is vented from the sensor through the porous electrolyte membrane; and
    determining the concentration of nitrogen oxides (NOX) and/or ammonia (NH3) based on the measured current.

2. The method of claim 1, wherein said gaseous oxidizing atmosphere comprises engine exhaust.

3. The method of claim 1, wherein said counter electrode comprises:
    lanthanide manganite perovskite material, doped with Ca, Sr, Ba, Fe, Co, Ni, Cu, Zn, Mg or a mixture thereof;
    lanthanide ferrite perovskite material, doped with Ca, Sr, Ba, Mn, Co, Ni, Cu, Zn, Mg or a mixture thereof;
    lanthanide cobaltite perovskite material, doped with Ca, Sr, Ba, Mn, Fe, Ni, Cu, Zn, Mg or a mixture thereof;
    lanthanide nickelate perovskite material, doped with Ca, Sr, Ba, Mn, Fe, Co, Cu, Zn, Mg or a mixture thereof;
    lanthanide cuprate perovskite material, doped with Ca, Sr, Ba, Mn, Fe, Co, Ni, or a mixture thereof; or
    a metal material comprising Ni, Fe, Cu, Ag, Au, Pd, Pt, or Ir, or an alloy or a cermet thereof.

4. The method of claim 3, wherein the porous electrolyte layer comprises cerium oxide doped with Y, Nd, Sm, Gd, La or mixtures thereof.

5. The method of claim 1, wherein oxygen gas from the counter electrode is not vented through the counter electrode.

6. The method of claim 1, wherein the sensor is controllably maintained at a temperature of about 200 to 550° C.

7. The method of claim 1, wherein the applied bias is about 0.1 to about 0.4 volt.

8. The method of claim 1, wherein the sensor exhibits enhanced reduction of oxygen molecules at the sensing electrode in the presence of one or more nitrogen oxides and a resulting increase in oxygen ion flux through the cell in proportion to a concentration of nitrogen oxides in the oxidizing atmosphere, wherein the concentration of nitrogen oxides is determined based on the measured current.

9. The method of claim 8, wherein the sensor exhibits at least sixty percent of its equilibrium response to the presence of nitrogen oxides in less than 200 milliseconds.

10. The method of claim 1, wherein the sensor generates an electrical signal as a function of $NO_X$ and/or ammonia $NH_3$ concentration in an oxygen-containing gas stream, in the absence of additional sensing electrodes or oxygen pumping currents.

11. The method of claim 1, wherein the electrode layers are symmetrically opposed to one another on opposite surfaces of the electrolyte.

12. The method of claim 1, wherein the sensor further comprises a substrate comprising an insulating ceramic or a metal or cermet material coated with an insulator.

13. The method of claim 12, wherein the sensor further comprises an electrical heating element applied to or embedded in the substrate, electrically isolated from the electrode layers and the electrolyte of the electrochemical sensor, wherein the heater is used to controllably maintain the temperature of the sensor.

14. The method of claim 1, wherein the sensor further comprises a protective layer of a porous material.

15. The method of claim 1, wherein the sensing electrode further includes a catalytic or electrocatalytic promoter.

16. The method of claim 15, wherein the catalytic or electrocatalytic promoter comprises an alkali metal or an alkaline earth metal.

17. The method of claim 15, wherein the catalytic or electrocatalytic promoter comprises one or more of K, Na, Li, Mg, Ca, Sr, Ba, Co, and Fe.

18. The method of claim 1, wherein the sensing electrode further includes an inhibitor which decreases electrical resistance of the cell in the absence of $NO_X$, wherein the inhibitor comprises one or more of Cl, F, K, Ba, Na, Ca, La, Sr, Mg and Li.

19. The method of claim 15, wherein the catalytic or electrocatalytic promoter comprises one or more of Ag, Au, Ru, Ir, Ni, Fe, Cu, Sn, V, Rh, Co, W, Mo, U, Zn, Mn, Cr and Nb.

20. An electrochemical sensor for the amperometric detection of gas species, comprising:
    an ionically conducting, porous electrolyte, said electrolyte having sufficient porosity and configured such that, during use, oxygen is vented from the sensor through the electrolyte, the electrolyte comprising—
cerium oxide doped with Ca, Sr, Sc, Y, Pr, Nd, Pm, Sm, Eu, Gd, Tb, Dy, Ho, Er, Tm, Yb, La, or a mixture thereof;
zirconium oxide doped with Ca, Mg, Sc, Y, Ce, or a mixture thereof;
bismuth oxide doped with Y, V, Cu, Er or a mixture thereof; or
lanthanum gallium oxide doped with Sr, Mg, Zn, Co, Fe or a mixture thereof;
a sensing electrode comprising a continuous network of a ceramic phase and a metallic phase, wherein the ceramic phase comprises Gd or Sm-doped ceria, and the metallic phase comprises Pt, Pd, or an alloy or mixture thereof; and
a counter electrode comprising
lanthanide manganite perovskite material, doped with Ca, Sr, Ba, Fe, Co, Ni, Cu, Zn, Mg or a mixture thereof;
lanthanide ferrite perovskite material, doped with Ca, Sr, Ba, Mn, Co, Ni, Cu, Zn, Mg or a mixture thereof;
lanthanide cobaltite perovskite material, doped with Ca, Sr, Ba, Mn, Fe, Ni, Cu, Zn, Mg or a mixture thereof;
lanthanide nickelate perovskite material, doped with Ca, Sr, Ba, Mn, Fe, Co, Cu, Zn, Mg or a mixture thereof;
lanthanide cuprate perovskite material, doped with Ca, Sr, Ba, Mn, Fe, Co, Ni, or a mixture thereof; or
a metal material comprising Ni, Fe, Cu, Ag, Au, Pd, Pt, or Ir, or an alloy or a cermet thereof
wherein the sensing and counter electrode layers are positioned on opposite sides of the porous electrolyte such that, during use, oxygen ion current flows through a thickness of the porous electrolyte when a bias is applied to the sensor.

21. The electrochemical sensor of claim 20, wherein the porous electrolyte comprises ionically conducting cerium oxide doped with Ca, Sr, Sc, Y, Pr, Nd, Pm, Sm, Eu, Gd, Tb, Dy, Ho, Er, Tm, Yb, La or a mixture thereof.

22. The electrochemical sensor of claim 21, wherein the porous electrolyte is ionically conducting and comprises cerium oxide doped with Y, Nd, Sm, Gd, La or mixtures thereof; and the counter electrode is electronically conducting.

23. The electrochemical sensor of claim 21, wherein the porous electrolyte is ionically conducting and comprises Sm-doped cerium oxide electrolyte; and the counter electrode is an electrically conducting and comprises Lanthanum Strontium Cobalt Ferrite.

24. The amperometric ceramic electrochemical sensor of claim 20, wherein the sensor is configured to be operable in an oxidizing atmosphere and under a first applied bias to exhibit enhanced reduction of oxygen molecules at the sensing electrode in the presence of one or more nitrogen oxides ($NO_x$) and a resulting increase in oxygen ion flux through the cell and is operable in the oxidizing atmosphere and under a second applied bias different from the first applied bias to exhibit enhanced reduction of oxygen molecules at the sensing electrode in the presence of $NH_3$ and a resulting increase in oxygen ion flux through the cell.

25. An amperometric sensor, comprising
a first amperometric sensor according to claim 20, wherein the first sensor is configured to be operable in an oxidizing atmosphere and under a first applied bias to exhibit enhanced reduction of oxygen molecules at the sensing electrode in the presence of one or more nitrogen oxides ($NO_x$) and a resulting increase in oxygen ion flux through the first sensor; and
a second amperometric sensor, wherein the second sensor is configured to be operable under a second applied bias different from the first applied bias to exhibit enhanced reduction of oxygen molecules at the sensing electrode in the presence of $NH_3$ and a resulting increase in oxygen ion flux through the second sensor.

26. The electrochemical sensor of claim 25, further comprising a substrate for the first and second electrochemical sensors, the substrate comprising insulating ceramic or a metal or cermet material coated with an insulator.

27. The electrochemical sensor of claim 21, wherein the porous electrolyte comprises Gadolinium-doped ceria (GDC) or Samarium-doped ceria (SDC).

28. The electrochemical sensor of claim 21, further comprising a yttrium-doped zirconia, aluminum oxide ($Al_2O_3$), magnesium oxide (MgO), or magnesium aluminate ($MgAl_2O_4$) substrate.

29. The electrochemical sensor of claim 28, further comprising an electrical heating element applied to or embedded in the substrate, electrically isolated from the electrodes and the porous electrolyte.

30. The electrochemical sensor of claim 28, wherein the sensing electrode further includes a catalytic or electrocatalytic promoter.

* * * * *